US008647309B2

(12) United States Patent
Harms et al.

(10) Patent No.: US 8,647,309 B2
(45) Date of Patent: Feb. 11, 2014

(54) MEDICATION DELIVERY DEVICE

(75) Inventors: Michael Harms, Oberursel (DE); James Robert Howarth, Cambridge (GB); Robin Craig Cocker, Yorkshire (GB); George Richard Gregory, Hertfordshire (GB); Anthony Raymond Charpentier, Warwickshire (GB); Michael Strehl, Pfreimd (DE); Udo Leuschner, Regensburg (DE); Norbert Besenhardt, Teublitz (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 467 days.

(21) Appl. No.: 12/194,709

(22) Filed: Aug. 20, 2008

(65) Prior Publication Data
US 2009/0275916 A1 Nov. 5, 2009

(30) Foreign Application Priority Data

May 2, 2008 (EP) ..................................... 08008352

(51) Int. Cl.
*A61M 5/00* (2006.01)
(52) U.S. Cl.
USPC ............ 604/207; 604/208; 604/209; 604/211
(58) Field of Classification Search
USPC .......................... 604/218–231, 506, 207–211
See application file for complete search history.

(56) References Cited

U.S. PATENT DOCUMENTS

| 5,827,232 A | 10/1998 | Chanoch et al. |
| 6,235,004 B1 | 5/2001 | Steenfeldt-Jensen et al. |
| 7,850,662 B2 * | 12/2010 | Veasey et al. ................. 604/207 |
| 2007/0123829 A1 * | 5/2007 | Atterbury et al. ............. 604/207 |

FOREIGN PATENT DOCUMENTS

| EP | 0 554 996 | 10/1996 |
| EP | 1 250 167 | 7/2005 |
| WO | WO 97/10864 | 3/1997 |
| WO | 2004/007003 A1 | 1/2004 |
| WO | WO 2004/078239 A1 | 9/2004 |
| WO | WO 2006/128794 A2 | 12/2006 |
| WO | 2007/006662 A1 | 1/2007 |
| WO | 2007/017053 A1 | 2/2007 |
| WO | WO 2007/017052 A1 | 2/2007 |
| WO | WO 2008/074897 A1 | 6/2008 |

OTHER PUBLICATIONS

U.S. Appl. No. 12/194,705, filed Aug. 20, 2008, Harms.
U.S. Appl. No. 12/194,707, filed Aug. 20, 2008, Harms.

* cited by examiner

*Primary Examiner* — Kevin C Sirmons
*Assistant Examiner* — Imani Hayman
(74) *Attorney, Agent, or Firm* — McDonnell Boehnen Hulbert & Berghoff LLP

(57) ABSTRACT

The present invention relates to a medication delivery device, to dosing mechanisms suitable for use in such medication delivery device, in particular in pen-type injectors, preferably having a dose setting member and a drive device enabling the dose setting and the administration of a medicinal product from a multi-dose medication cartridge, to methods using such device, and to methods of manufacturing and assembly of such device.

35 Claims, 8 Drawing Sheets

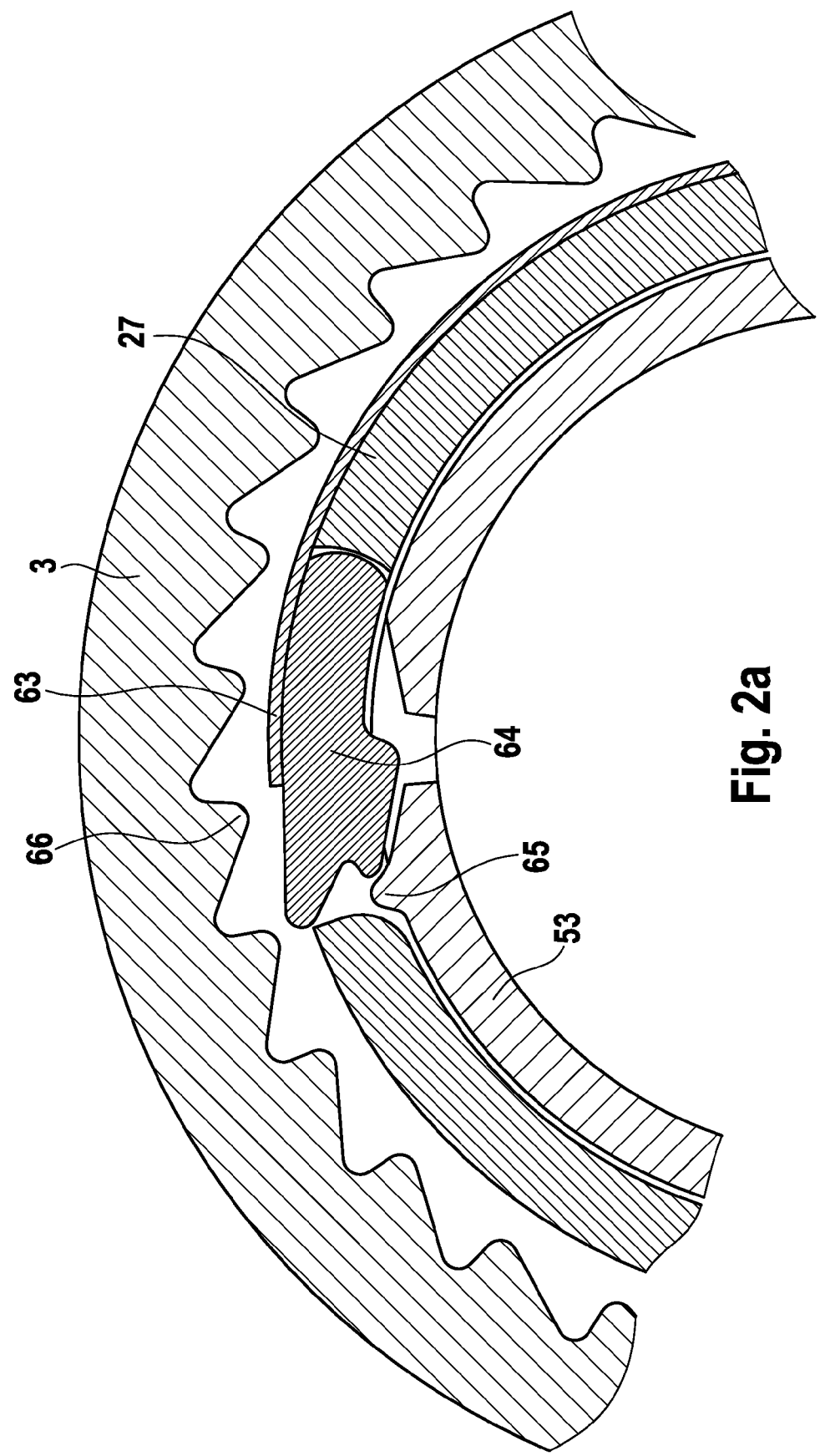

MEDICATION DELIVERY DEVICE

The present invention relates to a medication delivery device, a use of the device and a method of manufacturing or assembling the device. The invention refers particularly to dosing mechanisms suitable for use in such medication delivery devices, in particular in pen-type injectors, preferably having a dose setting member and a drive device enabling the dose setting and the administration of a medicinal product from a multi-dose medication cartridge. In particular, the present invention relates to such medication delivery devices where a user may set and dispense a dose of medication to be delivered from a multi-dose cartridge. Most preferably, the medication delivery device comprises a multi-dose medication cartridge which can be replaced when the medication has been fully dispensed.

The present invention further relates to a dosing mechanism for a medication delivery device, and particularly to a dosing mechanism comprising a dose setting limiting mechanism with a dose limiting member which prevents the setting of a dose of medication which exceeds a maximum amount of medicament to be dispensed from a medication receptacle, essentially the total amount of medication contained in the medication receptacle of the medication delivery device. Most preferably the dose limiting member interacts (e.g. moves into abutment) with a stop element of the piston rod of the medication delivery device in order to limit the movement of a dose setting member for increasing a set dose of medication to be delivered when a user tries to set a dose exceeding the content remaining in the medication receptacle.

Such medication delivery devices have application where regular injections by persons without formal medical training occur, i.e., patients. This is increasingly common amongst those having diabetes where self-treatment enables such persons to conduct effective management of their diabetes.

These circumstances set a number of requirements for medication delivery devices of this kind. The device must be robust in construction, yet easy to use in terms of the manipulation of the parts, understanding by a user of its operation and the delivery of the required dose of medicament. Dose setting must be easy and unambiguous. In the case of those with diabetes, many users will be physically infirm and may also have impaired vision requiring the dosing mechanism to have a drive device which requires a low dispensing force and the medication delivery device to have an easy to read dose setting display.

As a result of environmental and economical reasons this kind of medication delivery device has been developed to allow only a part of the device to be discarded after all the medicament has been delivered, usually the medication cartridge only. This provides the additional requirement for such a medication delivery device that the resetting of the drive mechanism, when a new cartridge is attached to or inserted into the medication delivery device, needs to be easy and unambiguous without the need for the user to touch any component of the drive mechanism directly, thereby reducing the possibility of damage to the drive mechanism through e.g. contamination.

A further requirement of multi-dose medication delivery devices with means for setting variable doses to be delivered is to indicate to a user if he is attempting to set a dose of medication having a larger size than what is remaining in the medication receptacle (e.g. a medication cartridge). The user should further be prevented from setting a dose which exceeds the amount of medication left in the cartridge of the medication delivery device to avoid the potentially dangerous situation of the user believing that the set dose has been entirely injected, even though this is not the case, because the set dose exceeded the amount of medication left in the medication receptacle.

User operated medication delivery devices are well known within the medical field. Furthermore some medication delivery devices with special end-of-content mechanisms are also known in the art.

EP 1250167 B1 discloses a limiting mechanism that prevents setting of a dose that exceeds the amount of liquid left in a cartridge of an injection device. WO 2006/128794 A2 describes an injection device comprising a track and a track follower which track follower is moved along in the track when setting a dose and engages an end-wall of the track when the summarized set doses equal the initial amount of liquid in the reservoir thereby preventing a user from setting a dose larger than the remaining content of the reservoir. WO 2007/017052 A1 is also directed towards a mechanism for preventing setting of a dose which exceeds the amount of medicament in a reservoir in an injection device.

All of these dose setting limiting mechanisms known in the art have the drawback e.g. that they do not allow or at least hinder the resetting of the medication delivery device after the empty reservoir has been replaced by a full reservoir. For resetting such a device the piston rod and the limiting mechanism have to be moveable back into their initial positions without having to overcome a large resistance and with the smallest possible effort for the user.

BRIEF DESCRIPTION OF THE DRAWINGS

FIGS. 2a and 2b show schematically a cut-out of a medication delivery device according to the present invention comprising at least one locking member.

Figure 1A:
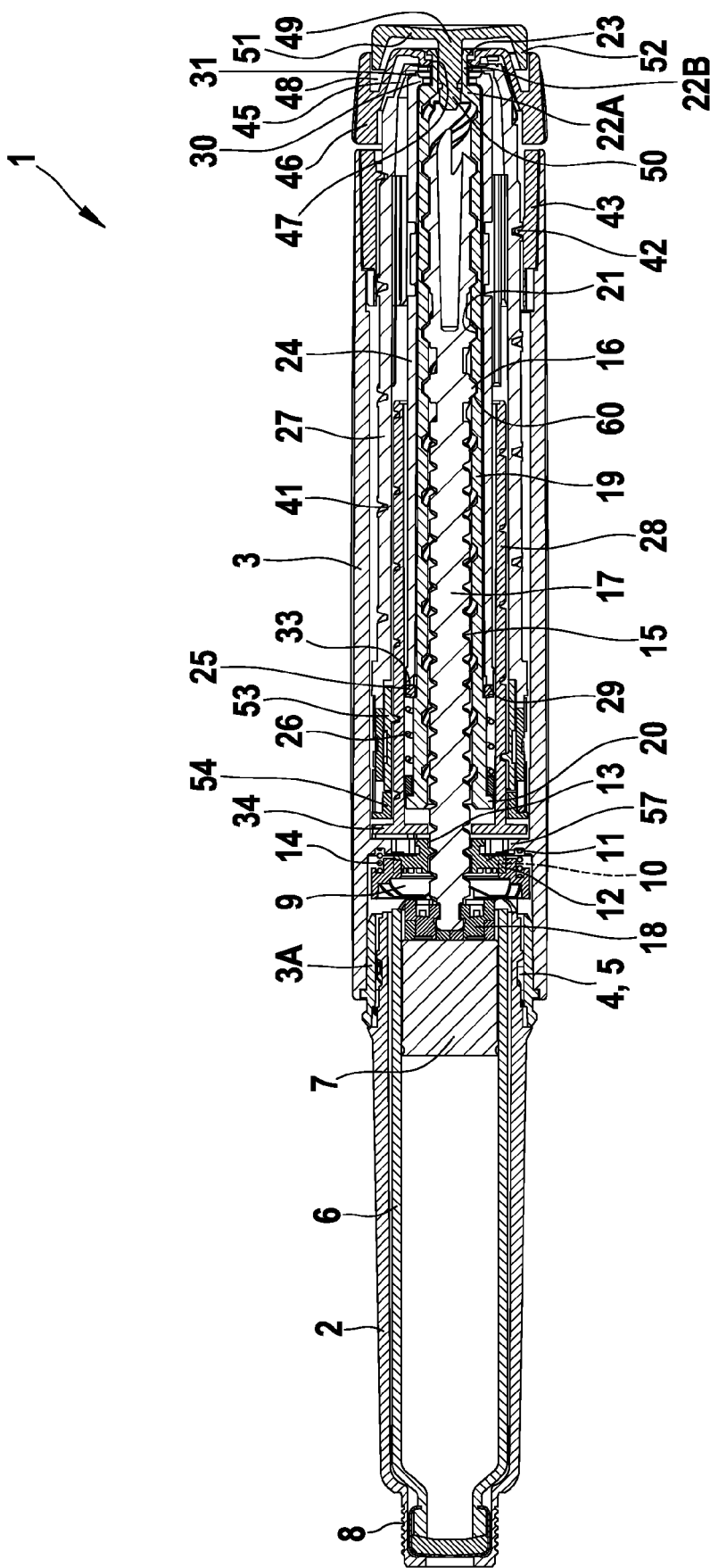
FIGS. 1a to 1c show a cross-sectional view of one embodiment of a medication delivery device according to the invention in three different states.

The object of the invention is to avoid the disadvantages of known medication delivery devices, particularly to provide an alternative dose setting limiting mechanism, most preferably an end-of-content mechanism which can be integrated into a flexible reset mechanism for use in a medication delivery device by means of which the medication delivery device can be reset for re-use when the medication cartridge is replaced.

Another object of the invention is to provide a dose setting limiting mechanism which securely limits the dose setting corresponding to the amount of medicament left in the medication receptacle of the medication delivery device, in particular by locking the dose setting member with the housing, thereby preventing the further movement of the dose setting member in a dose increasing direction with respect to the housing.

The medication delivery device according to the present invention provides a valuable technical alternative for known medication delivery devices. The medication delivery device according to the present invention e.g. has the advantage that the dose setting limiting mechanism securely and precisely limits the setting of a dose corresponding to the maximum amount of medicament to be dispensed from a medication receptacle, especially by the direct interaction of the dose limiting member with the piston rod the position of which is directly related to the amount of medicament left in the medication receptacle. Another advantage of the present invention is that the piston rod can be driven back into the device body when a new cartridge is attached, without the user having to touch any part of the dosing mechanism in particularly without touching any component of the dose setting limiting mechanism, e.g. the dose limiting member. The medication delivery device according to instant invention further provides the advantage of an easy replacement of the medication cartridge almost without application of pressure on the bung of the cartridge during resetting of the device and therefore without pressurization of the medication within the cartridge before the first setting and dispensing of a dose.

According to the invention, a medication delivery device is provided, comprising:
  a medication receptacle,
  a dosing mechanism comprising
    a piston rod which is moveable in a distal direction for medication delivery
    a drive device for moving the piston rod in the distal direction for medication delivery,
    a dose setting member for setting a dose of medication to be delivered and
    a dose limiting member which prevents the setting of a dose of medication which exceeds an amount of medication contained in the medication receptacle and
  a housing which houses at least part of the dosing mechanism.
  The dose limiting member is designed for axial movement in a proximal direction with respect to the piston rod during dose setting and the dose limiting member comprises a first stop element and the piston rod comprises a second stop element, the first and second stop elements stopping an axial movement of the dose limiting member in the proximal direction with respect to the piston rod when the first and second stop elements catch, thereby limiting a movement of the dose setting member for increasing a set dose of medication to be delivered, wherein the dose limiting member and the piston rod only interact directly, when the first and second stop elements catch.

Accordingly, the dose limiting member and the piston rod do not interact directly during the normal use (dose setting and dose delivery) of the medication delivery device as long as the amount of medication within the medication receptacle is sufficient. Only when the user attempts to set a dose which exceeds the amount of medication left in the medication receptacle, the first and second stop elements of the dose limiting member and the piston rod, respectively, catch (e.g. engage or abut), resulting in a direct interaction of the dose limiting member and the piston rod. This interaction of the piston rod and the dose limiting member only in this one case of the "last dose situation" of the device has the advantage, that there is also no interaction between the dose limiting member and the piston rod during resetting of the device (i.e. moving back the piston rod to its initial position when inserting a new cartridge into the device). Therefore, the dose limiting member does not prevent or hinder the resetting of the medication delivery device.

According to a preferred embodiment of the present invention the dose limiting member is engaged with the dose setting member, the dose limiting member stopping a dose increasing movement of the dose setting member when the axial movement of the dose limiting member is stopped. The direct engagement has the advantage of the dose limiting member being able to stop the dose increasing movement of the dose setting member directly and not indirectly via other components of the device. Preferably, the dose limiting member is engaged with the dose setting member by means of a thread or splines.

Alternatively and according to another preferred embodiment, the dose limiting member can e.g. be engaged with an insert of the dose setting member which is prevented from moving with respect to the dose setting member or which is provided for limited movement (i.e. limited axial and/or rotational movement) with respect to the dose setting member. Preferably, the dose limiting member is engaged with the insert of the dose setting member by means of a thread or splines.

According to a preferred embodiment of the present invention the dose limiting member is coupled to or engaged with the dose setting member
  so that the dose limiting member is moved in the proximal direction with respect to the housing and with respect to the piston rod during dose setting when the set dose of medication to be delivered is increased and
  so that the dose limiting member is moved in the distal direction with respect to the housing during medication delivery.

The dose limiting member can e.g. be engaged with the dose setting member via an internal thread of the dose setting member or engaged with a threaded insert of the dose setting member.

Preferably, the dose setting member is a dose dial sleeve which is threadedly engaged with the housing and therefore rotates and moves proximally with respect to the housing during setting of a higher dose, rotates and moves distally with respect to the housing during reducing the set dose and rotates and moves distally with respect to the housing during dose delivery.

The dose limiting member is preferably threadedly engaged with the dose setting member or with an insert of the dose setting member, it most preferably comprises an essentially tubular sleeve which is threadedly engaged with the dose setting member or with an insert of the dose setting member.

Preferably, the dose limiting member comprises an opening, wherein the piston rod extends through the opening and the first stop element is provided as a surface surrounding the opening. Most preferably, the dose limiting member comprises an internal flange which has an opening, wherein the piston rod extends through the opening and wherein the internal flange comprises the first stop element. The first stop element is preferably an abutment surface of the internal flange of the dose limiting member. As long as the first stop element does not catch the second stop element of the piston rod, a relative axial movement of the piston rod (within/through the opening of the flange) and the dose limiting member is allowed without interaction of the piston rod and the dose limiting member.

In some embodiments of the present invention the first stop element can comprise a set of teeth or an abutment surface on a flange.

In some embodiments the second stop element is a protrusion which extends radially from the piston rod, the axial position of the protrusion on the piston rod being related to the total amount of medicament to be dispensed from the medication receptacle. The protrusion may e.g. be an outer rim or lug. It is preferably designed such that it catches an abutment surface (e.g. of an internal flange) of the dose limiting member when a setting of a dose is attempted which exceeds the amount of medication contained in the medication receptacle, thereby stopping an axial movement of the dose limiting member in the proximal direction with respect to the piston rod.

According to a particularly advantageous embodiment of the invention the second stop element is the end of a thread on the piston rod. Preferably, the piston rod comprises two threaded regions, a first threaded region which does not influence axial movement of the dose limiting member and a second threaded region, wherein one end of a thread in the second threaded region forms the second stop element. In this embodiment the cross section of the second thread is preferably larger than the cross section of the first thread, the first thread passing through an opening of the dose limiting member without interaction of the piston rod with the dose limiting member and the second thread not passing through the opening but abutting the surrounding edge of the opening. Most preferably, the piston rod comprises two threaded regions, the two threaded regions having threads which are oppositely disposed.

According to a preferred embodiment of the present invention the dose limiting member is allowed to move axially and is prevented from rotation with respect to the housing. Preferably, the dose limiting member is splined to the housing and is thereby prevented from rotation with respect to the housing. Preferably, the dose limiting member is non-rotatable with respect to the housing and piston rod rotates during dose delivery with respect to the housing and with respect to the dose limiting member.

Preferably, the dose limiting member is positioned in the same position with respect to the housing prior to dose setting and after dose delivery, most preferably moving axially in one direction during the setting of a higher dose and in the other direction during the setting of a lower dose and/or during dose delivery. Preferably the distance of axial travelling of the dose limiting member in one direction with respect to the housing from an initial position to the set dose position during dose setting and the distance of axial travelling of the dose limiting member in the other direction with respect to the housing from the set dose position to the initial position during dose delivery are essentially the same. According to a particularly advantageous embodiment of the invention, the dose limiting member and the piston rod travel essentially the same distance in the distal direction during medication delivery.

In some embodiments the medication delivery device according to the present invention further comprises a drive device which is engaged with the piston rod and releasably engaged with the dose setting member. Preferably, the piston rod comprises two threaded regions, the two threaded regions having threads which are oppositely disposed, wherein a second threaded region is provided for threaded engagement with the drive device, preferably a drive sleeve. The first threaded region can e.g. be provided for threaded engagement with a nut means which is non-rotatably attached with or integral of the housing. The releasable engagement between the drive device and the dose setting member (e.g. a drive sleeve and a dose dial sleeve) can e.g. be achieved by means of a clutch mechanism.

In some embodiments the medication delivery device according to the present invention further comprises a clutch means located between the dose setting member and the drive device (preferably between the dose dial sleeve and the drive sleeve) which is provided to releasably couple the drive device with the dose setting member, wherein when the dose setting member and the drive device are coupled, both are allowed to rotate with respect to the housing and when the dose setting member and the drive device are decoupled, rotation of the dose setting member with respect to the housing is allowed, whilst rotation of the drive device with respect to the housing is not allowed and axial movement of the drive device is allowed so that a force is transferred to the piston rod in the distal direction. When the dose setting member and the drive device are decoupled, rotation of the drive device with respect to the housing can e.g. be prevented by the drive device engaging another component of the medication delivery device which is non-rotateable with respect to the housing.

The medication delivery device according to the present invention can e.g. be designed such that the dose limiting member comprises a tubular part which surrounds the piston rod, the drive sleeve and the clutch means and which is surrounded by a dose dial sleeve.

According to a preferred embodiment of the present invention, the dosing mechanism comprises at least one locking member for locking the dose setting member with the housing, thereby preventing further rotation of the dose setting member with respect to the housing in a dose increasing direction, the locking member being activated when the first stop element of the dose limiting member catches the second stop element of the piston rod and when a force (e.g. a torque) is exerted on the dose setting member in the dose increasing direction. The catching of the two stop elements results in stopping the axial movement of the dose limiting member in the proximal direction and thus the dose limiting member stopping the dose increasing movement of the dose setting member. Any further force/torque exerted by the user on the dose setting member is transferred to the at least one locking member and moves the at least one locking member into a locking position in which it locks the dose setting member with the housing. This locking action is an additional feature to prevent a further dose increasing movement of the dose setting member (the dose setting member being stopped by the dose limiting member and by the locking member).

Preferably the locking member interacts directly with or is connected to (i.e. attached to, engaged with or an integral part of) an insert (preferably a threaded insert) of the dose setting member, which insert is in engagement (preferably in threaded engagement) with the dose limiting member and designed for (preferably limited) movement (i.e. axial movement and/or rotational movement) with respect to the dose setting member. This means that the insert and the dose setting member are moveable with respect to each other, but are preferably held in a certain position with respect to each other (e.g. by a biasing means) before the first and second stop elements catch. When the two stop elements abut (thereby preventing a further axial movement of the dose limiting member in the proximal direction), a further force/torque exerted by the user on the dose setting member in the dose increasing direction is preferably transmitted to the insert, thereby moving the insert so that it activates the locking member. The dose setting member can e.g. be allowed to perform a movement (preferably only a small movement) in a dose increasing direction with respect to the insert when the first and second stop elements abut, thereby moving the at least one locking member and at least one locking feature of the housing into engagement.

The medication delivery device may e.g. comprise at least one locking member which interacts directly with or is connected to (i.e. attached to, engaged with or an integral part of) the dose setting member. The locking member(s) can e.g. be separate parts which are each connected to the dose setting member via a swivel axis.

Preferably, the at least one locking member or at least one locking feature of the housing is held in a first deactivated position by a biasing means. In some embodiments the at least one locking member is swivelled out by means of at least one ramp feature when activated, thereby engaging at least one locking feature of the housing. For example, an insert of the dose setting member comprises the at least one ramp feature and the at least one locking member is connected to the dose setting member via a swivel axis. The dose setting member has at least one opening adjacent to the at least one locking member through which the at least one locking member and the at least one ramp feature of the insert can interact. The dose setting member performs a rotational movement in a dose increasing direction with respect to the insert when the end-of content mechanism is activated (e.g. when the first and second stop elements abut, the dose limiting member stopping a further movement of the insert) and the user exerts a further force/torque on the dose setting member in the dose increasing direction, thereby moving the dose setting member with respect to the insert and thus the at least one locking member (preferably against the force of a biasing means) over the at least one ramp feature of the insert, the locking member thereby swivelling out and engaging at least one locking feature of the housing. The at least one locking member is moved into engagement with the locking feature by the ramp feature preferably because the ramp feature slides along a protrusion of the locking member (which can e.g. also be ramp-shaped).

The locking member is preferably automatically (e.g. by the force of a biasing means) disengaged from the locking feature of the housing as soon as the set dose is reduced and/or the user no longer exerts a force/torque on the dose setting member in the dose increasing direction (e.g. when the set dose is dispensed). Preferably a biasing means is provided which holds the locking member in its (de-activated) initial position as long as the end-of-content mechanism is not activated. Most preferably the biasing means thereby also prevents the insert from being moved (e.g. rotated) with respect to the dose setting member (and vice versa) as long as the end-of-content mechanism is not activated, e.g. by pressing a locking member against the ascending slope of a ramp feature of the insert.

The locking members can, alternatively, be integral parts of an insert of the dose setting member, the locking members extending (radially) through openings in the dose setting member. The locking members can for example be made of a flexible material, e.g. a flexible polymeric material. The dose setting member performs a rotational movement in the dose increasing direction with respect to the insert when the end-of content mechanism is activated (e.g. when the first and second stop elements abut) and the user exerts a force on the dose setting member in the dose increasing direction, thereby moving the locking members against an edge of the openings, the locking members thereby swivelling out and engaging locking features of the housing.

According to a preferred embodiment of the present invention the at least one locking member is engaged with grooves or splines in the housing when the locking member is activated, thereby preventing rotation of the dose setting member with respect to the housing in the dose increasing direction.

According to one embodiment the at least one locking member is a hook which is hooked into a hooking feature of the housing when the locking member is activated, thereby preventing rotation of the dose setting member with respect to the housing in the dose increasing direction.

In some embodiments the locking member comprises at least one tooth, preferably a plurality of teeth, for engaging a locking feature of the housing, e.g. a component with a tooth, preferably with a plurality of teeth. The locking member is connected to (i.e. attached to, engaged with or an integral part of) or interacts directly with the dose setting member. The locking feature is connected to (i.e. attached to, engaged with or an integral part of) or interacts directly with the housing or with an insert of the housing such that a movement (i.e. a rotational and/or axial movement, preferably a rotational movement) of the locking feature with respect to the housing in a dose increasing direction is prevented. Therefore, a movement (i.e. a rotational and/or axial movement, preferably a rotational movement) of the locking member in the dose increasing direction with respect to the housing is prevented when the locking member and the locking feature are engaged, e.g. when the teeth of the locking member and the teeth of the dose limiting member are engaged, thereby preventing a further movement (i.e. a rotational and/or axial movement, preferably a rotational movement) of the dose setting member with respect to the housing in a dose increasing direction.

In this embodiment a biasing means is preferably located between the locking member and the locking feature for keeping the locking member and the locking feature disengaged, preferably the teeth of the locking member and the teeth of the locking feature disengaged, until the locking member is activated (e.g. when the first stop element of the dose limiting member abuts the second stop element of the piston rod and when a further force or torque is exerted on the dose setting member in the dose increasing direction).

According to a preferred embodiment of the present invention the locking member is a first toothed ring connected to a dose dial sleeve and the locking feature is a second toothed ring, the second toothed ring being prevented from rotation with respect to the housing, thereby preventing rotation of the dose dial sleeve with respect to the housing when the two toothed rings are engaged.

The dose dial sleeve preferably has a threaded insert which is engaged with the dose limiting member, the second toothed ring being prevented from moving axially with respect to the threaded insert and the threaded insert being provided for axial movement with respect to the dose dial sleeve when the first and second stop members catch and a further force is exerted on the dose dial sleeve in a dose increasing direction, the first and second toothed rings thereby being moved into engagement.

According to a preferred embodiment of the present invention the dose delivery device further comprises a cartridge which contains the medication, the cartridge comprising a piston which is moved in a distal direction by the piston rod for medication delivery, wherein the dose limiting member and/or the at least one locking member is provided to prevent setting of a dose of medication which exceeds a maximum amount of medication to be dispensed from the cartridge.

The present invention further refers to a medication delivery device comprising
  a medication receptacle (e.g. a cartridge filled with a liquid medication),
  a dosing mechanism comprising
    a dose setting member for setting a dose of medication to be delivered and
    a dose setting limiting mechanism (end-of-content mechanism) which prevents the setting of a dose of medication which exceeds a maximum amount of medication to be delivered from the medication receptacle and
  a housing which houses at least part of the dosing mechanism,
wherein the dose setting limiting mechanism comprises at least one locking member for locking the dose setting member with the housing, thereby preventing movement of the dose setting member with respect to the housing in a dose increasing direction.

The at least one locking member of this variant of the present invention can be activated e.g. when two components (for example two stop elements as described above or a track follower and an end wall) of the medication delivery device are moved into abutment or engagement during dose setting and when the user then exerts a further force on the dose setting member to move it further in the dose increasing direction. This force is preferably transferred to the locking member in order to be activated and to be brought into a locking state in which the locking member locks the dose setting member with the housing of the dose delivery device, thereby preventing movement (preferably preventing rotation) of the dose setting member with respect to the housing in the dose increasing direction.

In the locking state the at least one locking member can e.g. be radially engaged with the surrounding housing of the medication delivery device (preferably with a locking feature of the housing) or with another component of the device which is not allowed to move in the dose increasing direction with respect to the housing. Alternatively the at least one locking member can in a locking state be prevented from moving in a dose increasing direction (e.g. not allowed to rotate) with respect to the housing e.g. when the locking member is axially engaged with a locking feature of the housing, the locking member preferably being

- engaged with the dose setting member directly or
- an integral part of the dose setting member or
- engaged with another component which is engaged with the dose setting member.

The at least one locking member according to this embodiment of the present invention is preferably designed similarly to the locking members described above.

The locking feature of the housing can e.g. be
- engaged with the housing directly or
- an integral part of the housing or
- engaged with another component which is engaged with the housing.

According to one preferred embodiment, the locking feature of the housing is further engaged with a moveable insert of the dose setting member, the locking feature being prevented from moving axially with respect to the insert.

The term "medication delivery device" according to instant invention shall mean a single-dose or multi-dose, disposable or re-useable device designed to dispense a dose of a medicinal product, preferably multiple selected doses, e.g. of insulin, growth hormones, low molecular weight heparins, and their analogues and/or derivatives etc. Said device may be of any shape, e.g. compact or pen-type. Dose delivery may be provided through a mechanical (optionally manual) dosing mechanism or electrical dosing mechanism or electromechanical dosing mechanism or stored energy dosing mechanism, such as a spring, etc. Dose selection may be provided through a manual mechanism or electronic mechanism or electromechanical mechanism. Additionally, said device may contain components designed to monitor physiological properties such as blood glucose levels, etc. Furthermore, the said device may comprise a needle or may be needle-free. Preferably, the term "medication delivery device" shall mean a re-useable multi-dose pen-type device having mechanical and manual dose selection and dose delivery mechanisms, which is designed for regular use by persons without formal medical training such as patients. Preferably, the medication delivery device is of the injector-type. Most preferably the medication delivery device is designed to deliver a fluid medication.

The term "dose setting limiting mechanism" or "end-of-content mechanism" according to the present invention shall preferably mean any component and/or components and/or assembly designed to prevent the setting of a dose which exceeds a maximum amount of medication to be dispensed from the medication receptacle of the medication delivery device. Most preferably the term "dose setting limiting mechanism" or "end-of-content mechanism" according to the present invention shall preferably mean any component and/or components and/or assembly designed to prevent the setting of a dose which exceeds the amount of medication left in the medication receptacle at the time when the dose is set.

The term "medication receptacle" in the context of the present invention shall preferably mean a cartridge containing a medication or a cartridge assembly, most preferably a cartridge holder for receiving a cartridge containing a medication. Furthermore, the terms "medication receptacle" and "cartridge" and "cartridge assembly" are exchangeable in the context of the present invention. This means that by using the term "medication receptacle", any meaning of the terms "cartridge" or "cartridge assembly" is included, and vice versa.

The term "cartridge holder" according to instant invention shall mean any component and/or components designed to house a medicament cartridge containing a medication to be delivered by the medication delivery device. Said cartridge holder may be of any shape, e.g. cylindrical and/or tubular. In general, the cartridge holder may be unitary or a multipart component of a cylindrical tubular or non-tubular shape. It may be made of any suitable material known by a person skilled in the art, e.g. of a transparent material. Further the cartridge holder or an insert of the cartridge holder is preferably provided with engagement means, e.g. helical threads or part threads or bayonet or the like, on an external and/or internal surface of the distal end and/or proximal end of the cartridge holder or the insert designed for engagement with corresponding engagement means located on an exterior and/or interior surface of a housing, an insert of the housing and/or a needle assembly. In a preferred embodiment the cartridge holder is of a unitary tubular design having an external thread located at its proximal end.

The term "housing" according to instant invention shall preferably mean any exterior housing ("housing", "body", "shell") or interior housing ("insert", "inner body") having an engaging means, such as a helical thread, spline or any other suitable means known by a person skilled in the art. The housing may be designed to enable the safe, correct, and comfortable handling of the medication delivery device or any of its mechanisms. Usually, it is designed to engage with any of the inner components of the medication delivery device (e.g., a dosing mechanism, cartridge, plunger, piston rod), house, fix, guide, and/or protect by limiting the exposure to contaminants, such as liquid, dust, dirt etc. In general, the housing may be unitary or a multipart component of tubular or non-tubular shape. The exterior housing may also serve to house a cartridge from which a number of doses of a medicinal product may be dispensed.

The terms "stop element" or "stop means" according to instant invention shall mean any feature(s) and/or component(s) of the medication delivery device designed to prevent axial and/or rotational movement of any component and/or components at least in one direction. In a preferred embodiment of instant invention, the term "stop element" shall mean any feature perpendicular to the distal-proximal axis of the medication delivery device (particularly any planar surface feature perpendicular to the distal-proximal axis of the medication delivery device) designed to prevent axial movement of a component in one direction when this component abuts the perpendicular feature. According to another preferred embodiment of the present invention the term "stop element" shall mean any feature which provides a radial or rotational stop designed to prevent rotational movement of a component in one rotational direction when an abutment element of the component abuts the radial or rotational stop feature.

The term "dose limiting member" according to the present invention shall preferably mean a component ("end stop") of the dosing mechanism which prevents the setting of a dose which exceeds the amount of medication left in the medication receptacle. Preferably the dose limiting member is a component which is secured against rotation but allowed to move axially with respect to a housing and which shall prevent at least one component of the dosing mechanism from rotational and/or axial movement when a final dose has been set, thereby preventing the setting of a dose which exceeds the amount of medication left in the cartridge. Furthermore, the "dose limiting member" shall preferably have a helical thread on an exterior surface designed to engage with an interior helical thread of a dose dial sleeve of the dosing mechanism or of an insert of a dose dial sleeve of the dosing mechanism. Preferably the lead of an external helical thread of the said dose dial sleeve for threaded engagement with the housing shall be greater than the lead of the internal helical thread of the dose dial sleeve for threaded engagement of the said dose limiting member.

The term "engaging" according to instant invention shall mean the interlocking of two or more components of the dosing mechanism/medication delivery device, by means of e.g. a spline, thread, or meshed teeth connection, preferably the interlocking of threads of components ("threadedly engaged").

The term "engagement means" according to the present invention shall preferably mean any means known to those skilled in the art which can be used to engage two or more components of a medication delivery device, e.g. full or part threads, grooves, engaging elements which mesh with threads and/or grooves or means which form a bayonet lock.

The term "disengaging" according to instant invention shall mean the unlocking of two or more components of the dosing mechanism/medication delivery device. According to one example the term "disengaging" according to instant invention shall mean the unlocking of two or more components of the dosing mechanism/medication delivery device under the force of a biasing means. Two components can also be disengaged by the force of a user of the device, e.g. by a patient unscrewing the medication receptacle from the housing.

The terms "to interact directly" or "direct interaction" according to the present invention shall mean any direct interaction of two components of the medication delivery device which leads to a load/force transmission from one of the components to the other. The term "to interact directly" particularly comprises interactions of two components like one component driving a movement (axial movement and/or rotation) of the other component or like one component stopping or preventing a movement (axial movement and/or rotation) of the other component. Such a direct interaction requires an engagement or at least an abutment of the two components. However, if one component only moves along another component this mere contact between the two components is not interpreted as causing a direct interaction between the two components in the context of the present invention.

The term "biasing means" according to instant invention shall preferably mean any component that is provided for exerting a force on a component and/or components to ensure that the component and/or components are forced together (e.g. into engagement) or forced apart (e.g. out of engagement). Preferably the biasing means may be manufactured from any suitable flexible energy storage material known by a person skilled in the art (e.g. metal, rubber or plastics) and may take any suitable form, e.g., a spring.

The term "distal end" according to instant invention shall mean the end of the device or a component of the device which is closest to the dispensing end of the device. Preferably a needle assembly is provided at the distal end of the medication delivery device of the present invention the needle of which can be inserted into the skin of a patient for medication delivery. The distal direction is therefore the direction from the proximal towards the distal end.

The term "proximal end" according to instant invention shall mean the end of the device or a component of the device which is furthest away from the dispensing end of the device. Preferably a button is provided at the proximal end of the medication delivery device of the present invention which is pushed for dose delivery. The proximal direction is therefore the direction from the distal towards the proximal end.

The term "dose increasing direction" according to the present invention shall preferably mean a direction of movement of the dose setting member with respect to the housing when the set dose is increased. This movement may be an axial and/or a rotational movement of the dose setting member. Preferably the movement is an axial movement in the proximal direction, most preferably an axial movement in the proximal direction in combination with a rotational movement in one rotational direction (clockwise or counterclockwise). In the latter case the movement of the dose setting member in the dose increasing direction can be limited by stopping the movement in the proximal direction and/or by stopping the movement in the rotational direction. A force which is exerted by a user on the dose setting member in the dose increasing direction can e.g. be a torque exerted on the dose setting member with respect to the housing if the dose is increased by winding the dose setting member out of the housing.

The term "dosing mechanism" according to instant invention shall mean any component and/or components and/or assembly designed to allow a user to select and/or set a dose to be dispensed and/or to provide and/or to transmit a force necessary to dispense a dose of a medication. Said dosing mechanism may be composed of mechanical and/or electromechanical and/or electronic components. Additionally, the dosing mechanism may be housed by and/or engaged with the device housing or may be an independent assembly. The dosing mechanism of instant invention preferably comprises a piston rod and a drive device for moving the piston rod in the distal direction for medication delivery. Preferably, the dosing mechanism of instant invention comprises a drive sleeve and a dose dial sleeve. More preferably, the dosing mechanism of instant invention comprises a drive sleeve, a dose dial sleeve, a clutch means, a dose dial grip and a button means.

The term "piston rod" according to instant invention shall mean a component adapted to operate through/within the housing, designed to transmit axial movement (preferably towards the distal end) through/within the medication delivery device, preferably from a drive sleeve to the piston of the cartridge, for the purpose of discharging/dispensing a medication from the cartridge, preferably an injectable product. Said piston rod may be flexible or not. It may be a simple rod, a lead-screw, a part of a rack and pinion system, a part of a worm gear system, or the like. The "piston rod" shall further mean a component having a circular or non-circular cross-section. It may be made of any suitable material known by a person skilled in the art.

In a preferred embodiment, the piston rod comprises at least two, more preferably two, external and/or internal helical threads (threaded sections). In another preferred embodiment of the piston rod according to instant invention, a first helical thread (first threaded section) is located at a distal end and a second helical thread (second threaded section) is located at a proximal end of the said piston rod, whereby the said threads of the threaded sections have opposite dispositions. In another preferred embodiment the piston rod of instant invention comprises at least two threaded sections with threads having the same leads and the same pitches at the distal and the proximal end. In yet another preferred embodiment of instant invention the lead and the pitch of the second helical thread of the piston rod shall be greater than the lead and the pitch of the first helical thread. More preferred, the ratio of the leads of the helical threads of the said first and the second helical threads is in the range of 1:1.01 to 1:20, even more preferred in the range of 1:1.1 to 1:10, most preferred 1:2.3. Preferably, one of the said threads (the thread of the second threaded section) is designed to engage with the drive sleeve. Preferably another of the said threads (the thread of the first threaded section) is designed to engage with a reset element, more preferably with a nut means. According to a most preferred embodiment of the present invention, a first external threaded section of the piston rod with a thread having a smaller lead is designed to engage with an internal thread of a nut means and a second external threaded section of the piston rod with a thread having a larger lead is designed to engage with an internal thread of a drive sleeve. In a further preferred embodiment of instant invention, the piston rod is provided with a stop element designed to limit the proximal axial movement of a dose limiting member. The stop element may e.g. be the start of one of the external threads of the piston rod.

The terms "dose setting member" and "dose dial sleeve" according to instant invention shall preferably mean a component of the medication delivery device which is directly or indirectly used to select/dial a dose of medication to be delivered.

Additionally or alternatively the dose setting member or dose dial sleeve is designed to indicate a selected dose of a dispensable product (medication). This may be achieved by use of markings, symbols, numerals, etc., e.g. printed on the external surface of a sleeve or an odometer, or the like. Most preferably the dose setting member or dose dial sleeve is marked by means of laser printing. In a preferred embodiment of the present invention, the dose setting member, in particular the dose dial sleeve is an essentially tubular component of essentially circular cross-section having either:
  both an internal and external thread, or
  an internal thread, or
  an external thread.

Preferably, the dose setting member, in particular the dose dial sleeve comprises an external thread for engaging an internal thread of the housing or of an insert of the housing. Preferably, the dose setting member, in particular the dose dial sleeve according to instant invention comprises an external helical thread having a lead, which is similar to, preferably the same as the lead of an internal helical thread of the drive sleeve. In a more specific embodiment of instant invention, the dose setting member or dose dial sleeve is provided with a plurality of radially extending stop members adapted to abut a corresponding plurality of radial stops provided within the housing or an insert of the housing. These radial stops are preferably provided for stopping a further winding of the dose setting member or dose dial sleeve out of the housing when a dose is set and/or for stopping the further winding of the dose setting member or dose dial sleeve into the housing when a dose has been dispensed.

The term "drive device" according to the present invention shall preferably mean any component and/or components and/or assembly designed to transmit a force to the piston rod for dispensing a dose of a medication. Said drive device may be composed of mechanical and/or electromechanical and/or electronic components. The drive device may be housed by and/or engaged with the housing or may be an independent assembly. Preferably, the drive device of instant invention comprises a drive sleeve. More preferably, the drive device of instant invention comprises a drive sleeve, a clutch means and a button means.

The term "drive sleeve" according to instant invention shall preferably mean any component for directly or indirectly driving the piston rod in a distal direction for medication delivery, most preferably for driving the piston rod directly. According to a preferred embodiment of the present invention, the drive sleeve is an essentially tubular component of essentially circular cross-section. In a preferred embodiment the drive sleeve is engaged with the piston rod. Preferably the drive sleeve comprises an internal thread for engaging an external thread of the piston rod. The drive sleeve is further preferably releasably coupled to a dose dial sleeve, most preferably by a clutch means.

The term "locking member" according to the present invention shall preferably mean any component(s) integral of, engaged with or connected to the dose setting member (or an insert of the dose setting member) which can be brought from a first deactivated state into a second activated state in which it is (they are) engaged with a locking feature of the housing or a locking feature of any component integral of, engaged with or connected to the housing. The locking member can e.g. be activated by being moved from a first into a second position in which it engages the locking feature or vice versa by the locking feature being moved from a first into a second position in which it engages the locking member. In this activated state the locking member indirectly or preferably directly locks the dose setting member with the housing, thereby preventing a dose increasing movement (preferably a dose increasing rotation) of the dose setting member with respect to the housing. Preferably the locking member is a component (e.g. a finger or hook) which is rotatable about an axis from the first deactivated state into the second activated state and vice versa. Alternatively the locking member can e.g. be a component integral of, engaged with or connected to the dose setting member (or an insert of the dose setting member) which has at least one tooth, preferably a plurality of teeth, and which can be engaged by a locking feature of the housing (preferably a ring having at least one tooth or tooth-shaped recess, preferably a plurality of teeth) which is axially moveable from a first position (deactivated state) into a second position (activated state) with respect to the dose setting member and vice versa.

The term "locking feature" according to the present invention shall preferably mean any component(s) integral of, engaged with or connected to the housing which is prevented from moving in a dose increasing direction with respect to the housing and which can be engaged by a locking member which is integral of, engaged with or connected to the dose setting member (or an insert of the dose setting member), thereby preventing a dose increasing movement (preferably a dose increasing rotation) of the dose setting member with respect to the housing. Preferably the locking feature is at least one protrusion, groove, spline, hook, tooth or the like on the inner surface of the housing or on the inner surface of an insert of the housing.

The term "thread" or "helical thread" according to instant invention shall preferably mean a full or part thread, e.g., a cylindrical spiral rib/groove, located on the internal and/or external surface of a component of the medication delivery device, having an essentially triangular or square or rounded section designed to allow continuous free rotational and axial movement between components. Optionally, a thread may be further designed to prevent rotational or axial movement of certain components in one direction by being non-overhaulable.

The term "lead" according to instant invention shall preferably mean the axial distance a nut would advance in one complete revolution; preferably "lead" shall mean the axial distance through which a component having a helical thread, i.e. dose dial sleeve, drive sleeve, piston rod, etc., of the dosing mechanism travels during one rotation. Therefore the lead is a function of the pitch of the thread of the relevant component.

The term "pitch" according to instant invention shall preferably mean the distance between consecutive contours on a helical thread, measured parallel to the axis of the helical thread.

One aspect of the present invention provides a medication delivery device according to instant invention for dispensing a medicinal product preferably for dispensing a pharmaceutical formulation (e.g. solution, suspension etc.) comprising an active compound selected from the group consisting of insulin, growth hormone, low molecular weight heparin, their analogues and their derivatives.

The medication delivery device according to the present invention can be a pen-type device and/or an injector-type device. The medication delivery device can comprise a needle or be a needle-free device.

The invention further refers to a method of manufacturing or assembling a medication delivery device according to one of the above-mentioned embodiments. This method preferably comprises the step of providing a dose limiting member as described above which is installed within a dosing mechanism.

According to the invention, the use of a medication delivery device according to one of the above-mentioned embodiments of a medication delivery device for dispensing a medicinal product is also provided. The use preferably comprises the dispensing of a pharmaceutical formulation (e.g. a liquid medication like a solution, a suspension etc.) comprising an active compound selected from the group consisting of insulin, growth hormone, low molecular weight heparin, their analogues, and their derivatives.

Figure 1B:
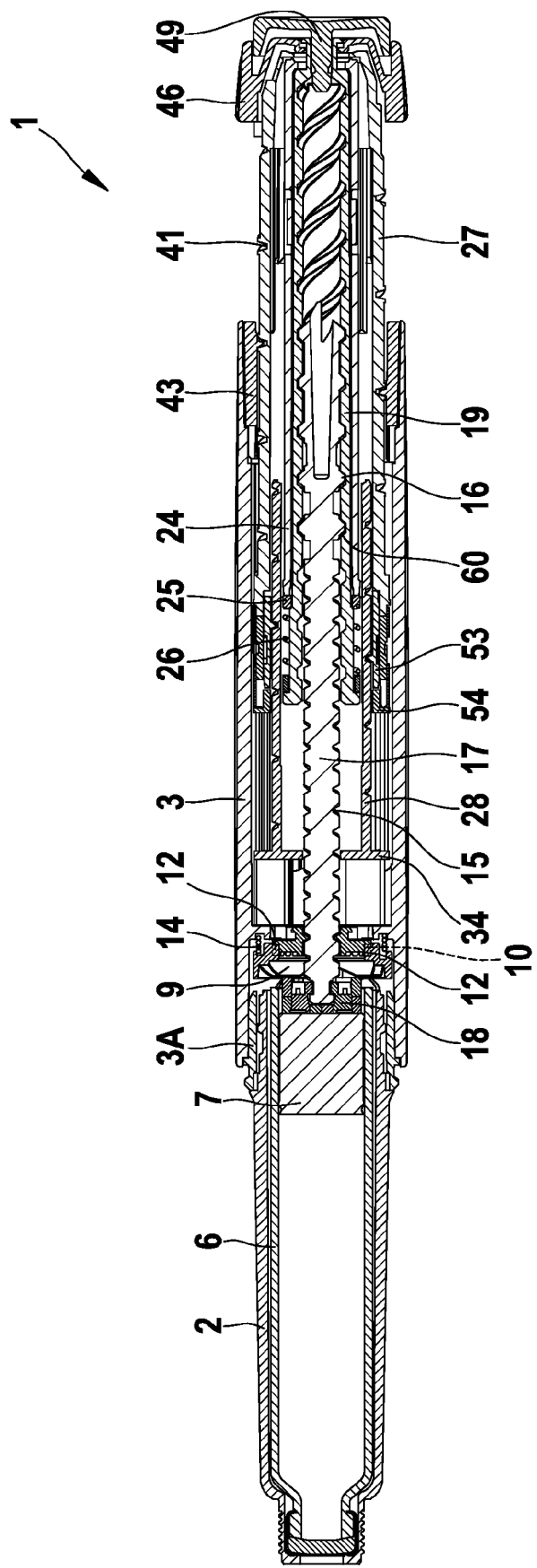
Figure 1C:
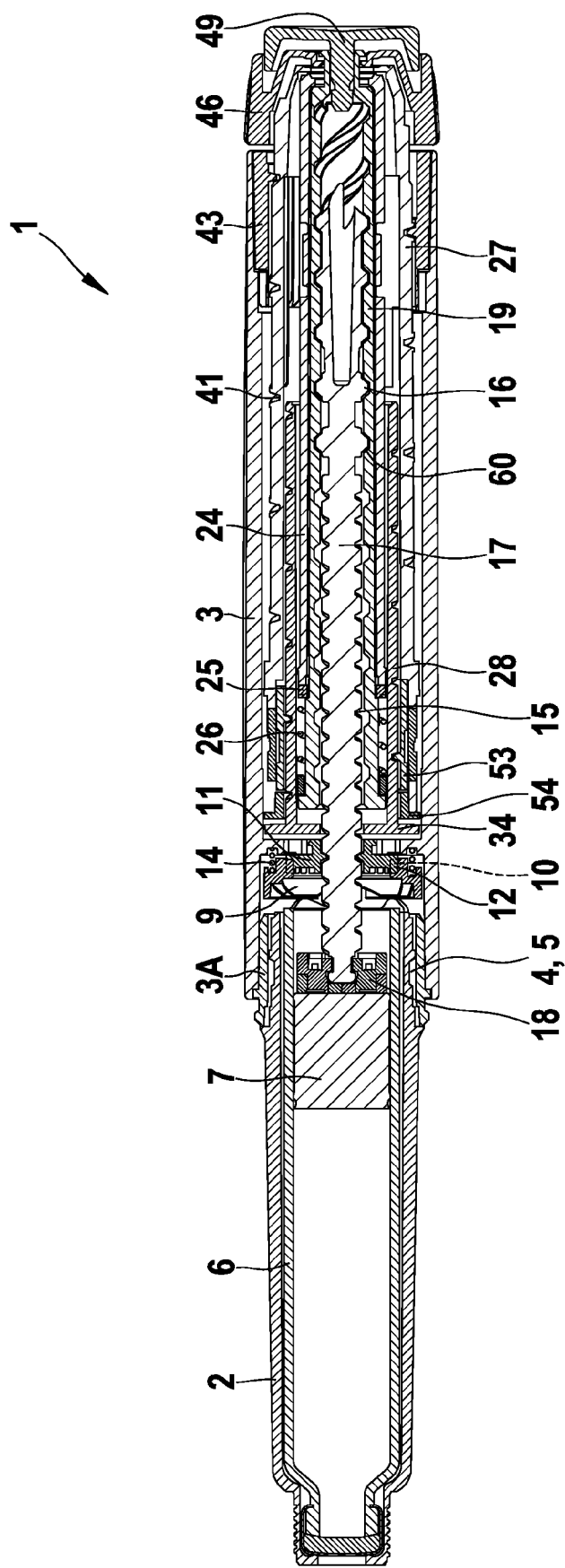
Figure 1D:
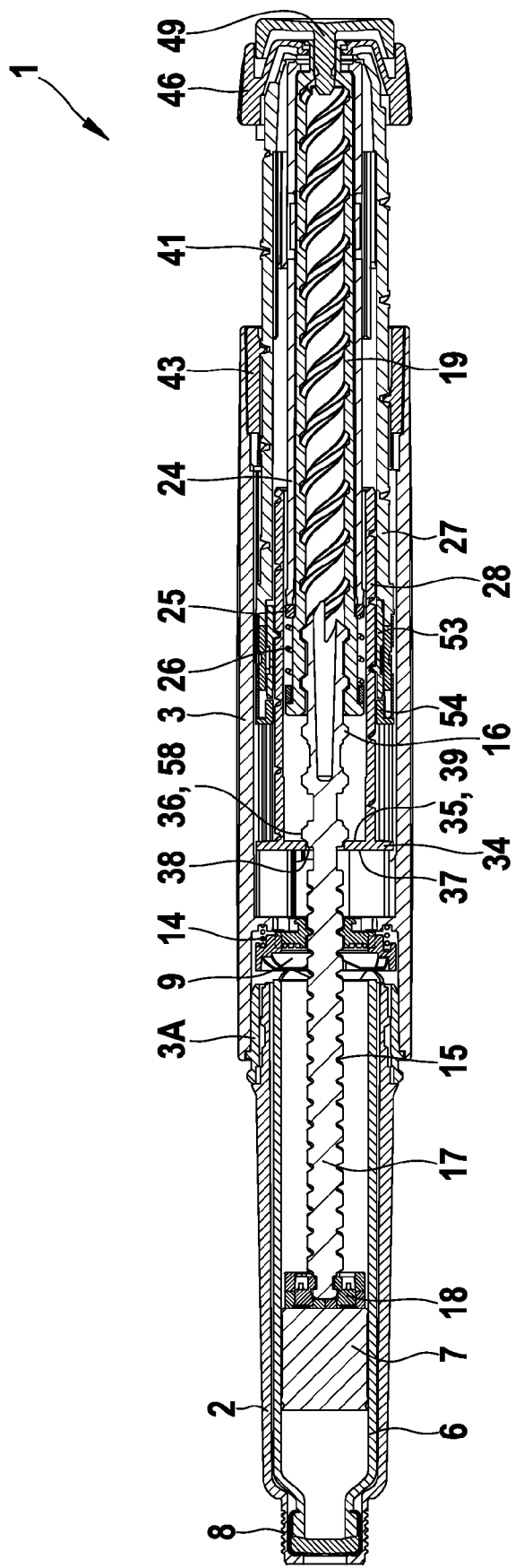
FIGS. 1d and 1e show the medication delivery device according to FIGS. 1a to 1c in a state in which the dose limiting member and the piston rod interact in order to prevent the setting of a higher dose.
Figure 1E:
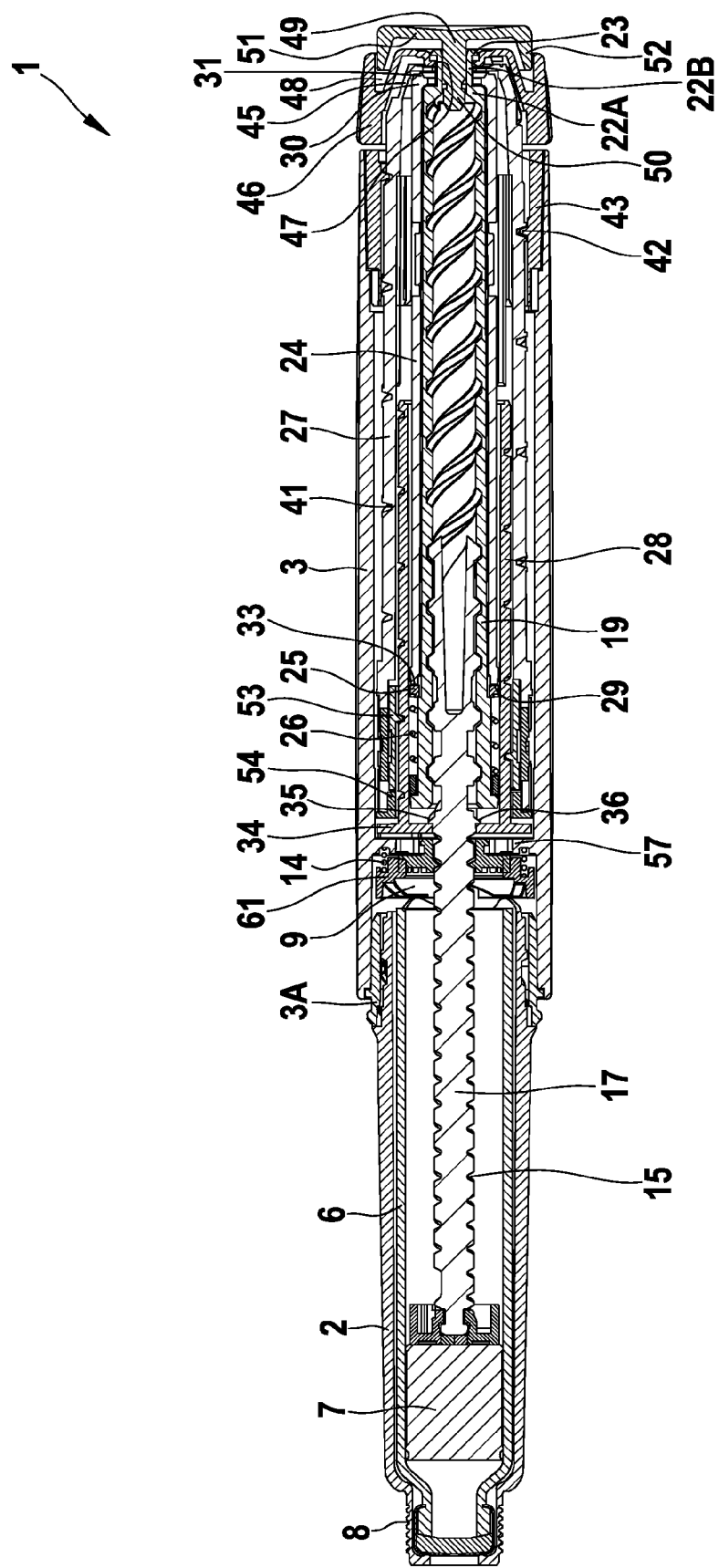

Without any limitation, the present invention will be explained in greater detail below with reference to the drawings in which:

FIGS. 1a to 1c show a cross-sectional view of one embodiment of a medication delivery device according to the invention in three different states;

FIGS. 1d and 1e show the medication delivery device according to FIGS. 1a to 1c in a state in which the dose limiting member and the piston rod interact in order to prevent the setting of a higher dose.

Figure 2B:
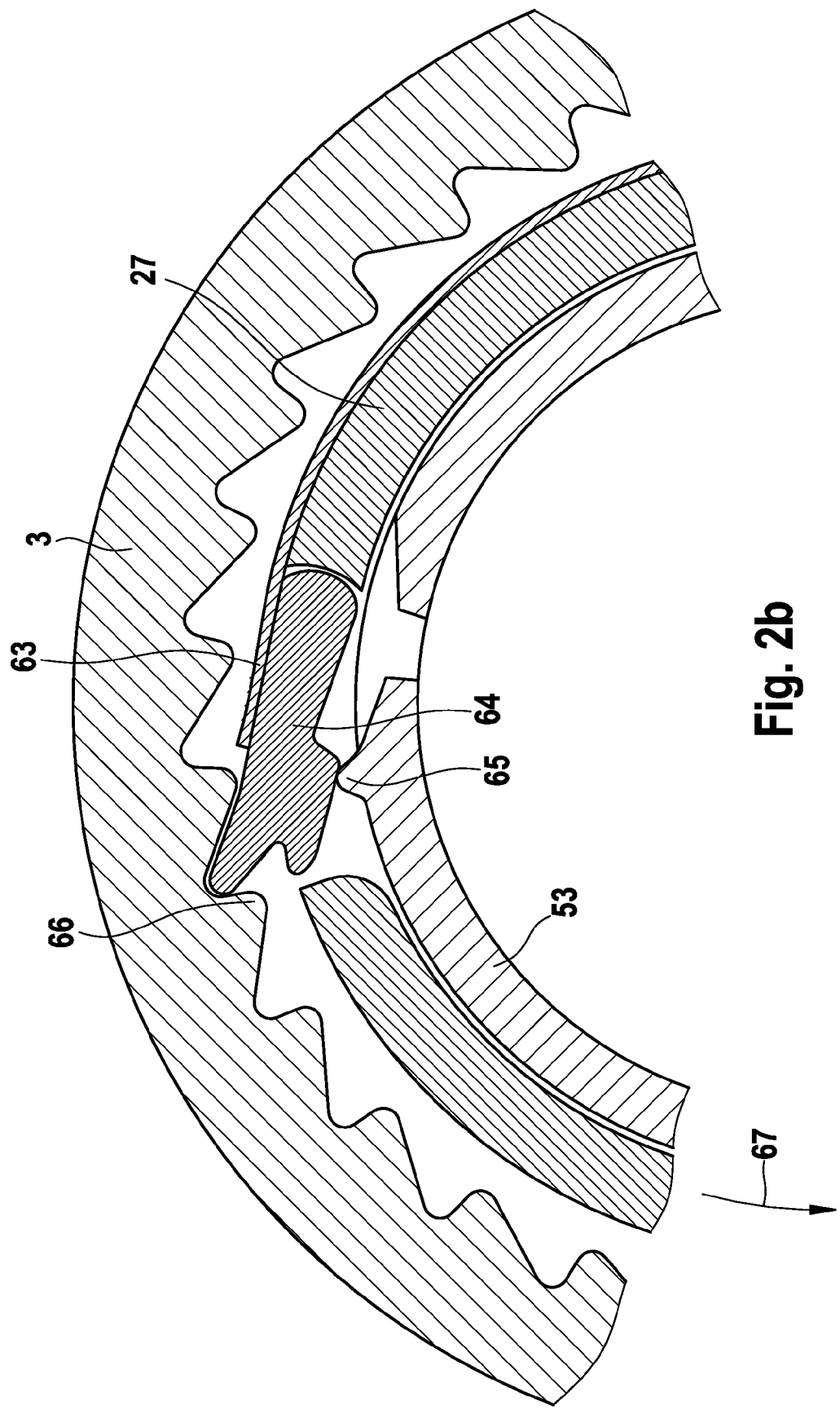

FIGS. 2a and 2b show schematically a cut-out of a medication delivery device according to the present invention comprising at least one locking member.

Figure 3:
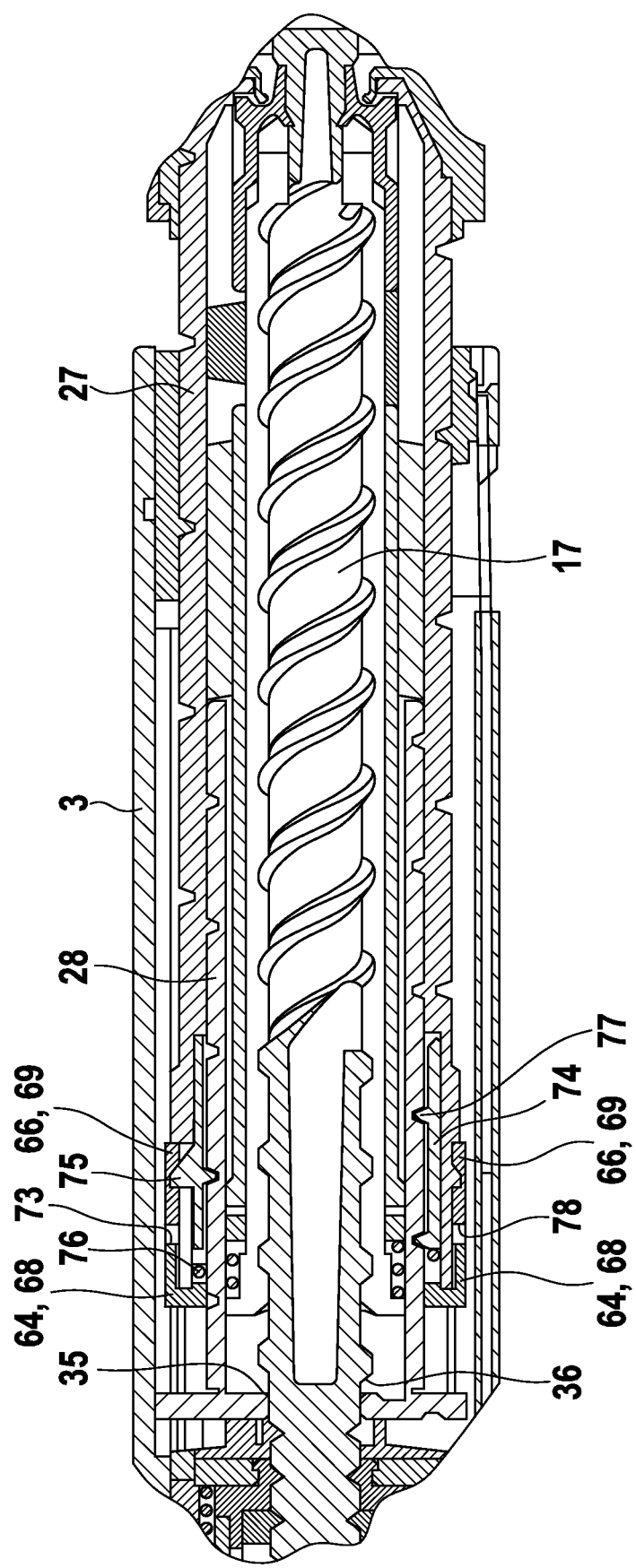
FIG. 3 shows a cut-out of cross-section of another embodiment of a medication delivery device according to the present invention comprising a locking member.

FIG. 3 shows a cut-out of cross-section of another embodiment of a medication delivery device according to the present invention comprising a locking member.

Referring first to FIGS. 1a to 1c, there is shown a medication delivery device in accordance with the present invention in three different positions.

The medication delivery device 1 comprises a cartridge holder 2 and a (exterior) housing 3. Preferably the housing 3 is lacquered. The distal end of the housing 3 is provided with an insert 3A which is immovably attached to the housing. The insert 3A is provided with second engagement means 4 for engaging first engagement means 5 of the cartridge holder 2. The proximal end of the cartridge holder 2 is provided with first engagement means 5 for engaging the second engagement means 4 of the insert 3A.

A cartridge 6 filled with medication from which a number of doses of the medication may be dispensed is provided in the cartridge holder 2. A piston 7 is retained in the cartridge 6.

A removable cap (not shown) can be releasably retained over the distal end of the cartridge holder 2. Preferably the cap comprises a clip which is snapped onto the cap. The cap can also be lacquered.

The distal end of the cartridge holder 2 is provided with suitable engaging means 8, such as a helical thread, bayonet or the like, for engagement with a suitable needle assembly (not shown) to enable medicament to be dispensed from the cartridge 6 and injected.

The medication delivery device 1 according to FIGS. 1a to 1e comprises a dosing mechanism which includes a piston rod 17 which is moveable in the distal direction for medication delivery. The piston rod 17 is of generally circular cross-section. A pressure foot 18 is located at the distal end of the piston rod 17. The pressure foot 18 is preferably made of two separate parts which are snapped together around a distal end portion of the piston rod 17. The pressure foot 18 is disposed to abut the proximal face of the piston 7 within the cartridge 6. The piston rod 17 is moveable in a distal direction by means of a drive device, thereby pushing the piston 7 to move axially within the cartridge 6 in the distal direction for medication delivery. A first thread 15 is formed at the distal end of the piston rod 17 (first threaded section 15). A second thread 16 is formed at the proximal end of the piston rod 17 (second threaded section 16). The first thread 15 and the second thread 16 are oppositely disposed. Preferably at least one of the first and second threads 15, 16 is a multi-start thread, most preferably both are two-start threads.

The drive device comprises a drive sleeve 19 which extends about the piston rod 17. The drive sleeve 19 is generally cylindrical. The drive sleeve 19 is provided at a distal end with a radially extending flange 20. A helical groove (thread) 21 extends along the internal surface of the drive sleeve 19. The second thread 16 of the piston rod 17 is adapted to work within the helical groove 21 of the drive sleeve 19.

A shoulder 22A and an extension 22B are formed at the proximal end of the drive sleeve 19. The extension 22B has reduced inner and outer diameters in comparison to the remainder of the drive sleeve 19. A proximal end of the extension 22B is provided with a radially outwardly directed flange 23.

A clutch 24 is disposed about the drive sleeve 19, between the drive sleeve 19 and a dose limiting member 28 (described below). The clutch 24 is located adjacent the proximal end of the drive sleeve 19. The clutch 24 is generally cylindrical and is provided at the distal end with a series of circumferentially directed saw teeth 29. Each saw tooth comprises a longitudinally directed surface and an inclined surface. Towards the proximal end of the clutch 24 there is located a radially inwardly directed flange 30. The flange 30 of the clutch 24 is disposed between the shoulder 22A of the drive sleeve 19 and the radially outwardly directed flange 23 of the extension 22B. The proximal end of the clutch 24 is provided with a plurality of saw teeth 31. The clutch 24 is keyed to the drive sleeve 19 by way of splines (not shown) to prevent rotation between the clutch 24 and the drive sleeve 19. The clutch 24 is provided with a plurality of flexible arms 32 (not shown) that engage a plurality of splines on an interior surface of a dose dial sleeve 27 (described below).

A clutch plate 25 and a biasing means 26 are located between the distal end of the clutch 24 and the proximal face of the radially extending flange 20 of the drive sleeve 19. In the illustrated embodiment, the biasing means 26 is a spring. The proximal face of the clutch plate 25 is provided with a series of circumferentially directed saw teeth 33. The clutch plate 25 is secured against rotation with respect to the housing 3. The saw teeth 33 of the clutch plate 25 interact with the saw teeth 29 at the distal end of the clutch 24 during dose setting (described below).

The dosing mechanism further comprises a dose limiting member 28 which prevents the setting of a dose of medication which exceeds the amount of medication contained in the cartridge 6. The dose limiting member 28 is disposed about the drive sleeve 19, between the drive sleeve 19 and the dose dial sleeve 27. The dose limiting member 28 is secured against rotation with respect to the housing 3 and is free to move axially with respect to the housing 3. At the distal end of the dose limiting member 28 a radially extending flange 34 is provided designed to engage with spline features (not shown) on an interior surface of the housing 3. In the illustrated embodiment, the external surface of the dose limiting member 28 is provided with a helical groove (thread) that extends the full length of the dose limiting member 28. The helical groove (thread) is engaged with a threaded insert 53 of the dose dial sleeve 27. An interior surface of the dose limiting member 28 is provided with a number of spline features (not shown). The clutch plate 25 is engaged with these spline features and thereby secured against rotation with respect to the housing 3

A dose dial sleeve 27 is provided between the clutch 24 and the housing 3. A helical groove (thread) 41 is provided about an outer surface of the dose dial sleeve 27. The housing 3 may be provided with a helical rib (thread) 42, adapted to be seated in the helical groove (thread) 41 of the dose dial sleeve 27. In the illustrated embodiment, the helical rib (thread) 42 is formed on an interior surface of an insert 43 of the housing 3. The threaded insert 43 is secured against rotation and axial movement with respect to the housing 3. The helical rib 42 extends for a single sweep of the inner surface of the insert 43. A proximal end of the dose dial sleeve 27 is provided with an inwardly directed flange in the form of a number of radially extending members 45.

The housing 3 is further provided with a window 40 (not shown) through which a part of the outer surface of the dose dial sleeve 27 may be seen. A visual indication of the dose that may be dialed is provided on the outer surface of the dose dial sleeve 27. The window 40 conveniently only allows a visual indication of the dose currently dialed to be viewed. The window can be designed such that it allows an enlarged visual indication of the dose currently dialled to be viewed by acting as a magnifying lens. Preferably the window 40 is filled with a transparent polymer. Most preferably the window 40 is part of an insert of the housing 3 which is made by two component injection moulding, wherein a section with a dark polymer surrounds a section with a transparent polymer. The insert is immovably fixed to the housing, e.g. by means of an adhesive tape.

The threaded insert 43 of the housing 3 is provided with a series of radial stop features 55, 56 (not shown). A distal end of the dose dial sleeve 27 is provided with a plurality of stop features 44 (not shown) which abut the stop features 56 of the insert 43 to prevent the dose dial sleeve 27 from being wound out of the housing 3 any further when a maximum dose has been set (e.g. 80 international units of insulin).

A dose dial grip 46 is disposed about an outer surface of the proximal end of the dose dial sleeve 27. An outer diameter of the dose dial grip 46 preferably corresponds to the outer diameter of the housing 3. The dose dial grip 46 is secured to the dose dial sleeve 27 to prevent movement therebetween. The dose dial grip 46 is provided with central opening 47. An annular recess 48, located in the proximal end of the dose dial grip 46, extends around the opening 47.

A button 49 is provided at the proximal end of the medication delivery device 1. In the illustrated embodiment of instant invention, the button 49 is of generally 'T' section, with a stem 50. The button 49 is preferably free to rotate with respect to the housing 3. Preferably the button 49 contains a washer (not shown) made of a friction reducing material (e.g. a friction modified polymer material) in order to reduce the friction between the button and dose dial grip 46 during dose delivery. The stem 50 of the button 49 extends through the central opening 47 in the dose dial grip 46 and through the inner diameter of the extension 22B of the drive sleeve 19. The stem 50 of the button 49 is retained for limited axial movement in the drive sleeve 19 and the clutch 24. In the illustrated embodiment, a head 51 of the button 49 is generally circular. A skirt 52 depends from a periphery of the head 51. The skirt 52 is adapted to be seated in the annular recess 48 of the dose dial grip 46.

An internal surface at the distal end of the dose dial sleeve 27 may be provided with a helical thread (not shown). In the illustrated embodiment, the helical thread of the dose dial sleeve 27 is provided on an internal surface of the threaded insert 53. The insert 53 is retained within the dose dial sleeve 27 by means of an end cap 54 secured to the distal end of the dose dial sleeve 27. The end cap 54 is secured against both rotational and axial movement with respect to the dose dial sleeve 27. The helical groove (thread) of the dose limiting member 28 is engaged with the threaded insert 53 of the dose dial sleeve 27.

The medication delivery device 1 further comprises nut means 11 which is a reset element and which has a series of face teeth 12 on a distal surface and a threaded circular opening 13. The first thread 15 of the piston rod 17 extends through and is threadedly engaged with the threaded circular opening 13 of the nut means 11. The nut means 11 is prevented from axial movement in the distal and/or proximal direction with respect to the housing 3, e.g. in the proximal direction by means of a web 57 within the housing 3. The web 57 can be a separate component or can be formed as part of the housing 3. In the devices shown in FIGS. 1a to 1c the nut means 11 is in an operational state in which the nut means 11 is prevented from rotation with respect to the housing 3 by means of a locking means 9 and therefore prevents proximal movement of the piston rod 17 during dose setting and dose delivery.

In the illustrated embodiment, the medication delivery device 1 is further provided with a locking means 9. The locking means 9 is secured against rotational movement with respect to the housing 3, but the locking means 9 is free for limited axial movement with respect to the housing 3 when the housing 3 is engaged with or disengaged from the cartridge holder 2. The locking means 9 is provided on a proximal surface with a series of face teeth 10 for engaging the face teeth 12 of the nut means 11. A biasing means 14, in the form of a spring, is provided between the proximal face of the locking means 9 and a web 57 within the housing.

In the shown embodiments according to FIGS. 1*a* to 1*c* the cartridge holder 2 (medication receptacle) comprises actuation means with ramps, the inclined surfaces of the ramps interacting with inclined surfaces of the locking means 9 when the cartridge holder 2 is being connected with the housing 3. By this interaction the locking means 9 is moved into engagement with the nut means 11. The actuation means thereby brings the nut means 11 in the operational state.

Accordingly, when the cartridge holder 2 (medication receptacle) is engaged with the distal end of the housing 3 the reset element 11 is in the operational state and when the cartridge holder 2 (medication receptacle) is disengaged from the distal end of the housing 3 the reset element 11 is in a resetting state In the operational state the reset element 11 is prevented from rotation with respect to the housing 3, the piston rod 17 being prevented from moving in a proximal direction, and in the resetting state the reset element 11 is allowed to rotate with respect to the housing 3, the medication delivery device being resettable by rotating the piston rod 17 in a second rotational direction and moving the piston rod 17 in the proximal direction.

Operation of the medication delivery device 1 in accordance with the present invention will now be described.

To dial a dose a user rotates the dose dial grip 46, thereby rotating the dose dial sleeve 27. During dose dialling the clutch 24 is engaged with the dose dial sleeve 27 via the saw teeth 31 at the proximal end of the clutch 24. As the clutch 24 is engaged with the rotating dose dial sleeve 27, the clutch 24 and the drive sleeve 19 rotate with the dose dial sleeve 27 because of the splined engagement of the clutch 24 and the drive sleeve 19.

Audible and tactile feedback of the dose being dialled is provided by the clutch plate 25 and the clutch 24. This feedback is provided by the saw teeth 29 of the clutch 24 gliding over the saw teeth 33 of the clutch plate 25 during the rotational movement of the clutch 24 with respect to the housing 3. During dose dialling, the clutch plate 25 is pushed axially towards the proximal end of the device by the biasing means 26, thus ensuring that the saw teeth 29 and 33 of clutch plate 25 and clutch 24 maintain contact. As the clutch plate 25 is secured against rotation by spline features on the interior surface of the dose limiting member 28, which is secured against rotation with respect to the housing, the clutch 24 rotates relative to the clutch plate 25 during dose setting. Due to the profile of the saw teeth 29 and 33, preferably triangular, the saw teeth 29 of the clutch 24 are able to glide over the saw teeth 33 of the clutch plate 25 as the clutch 24 rotates. Preferably, the ratio of the angular spacing of the saw teeth 29 of the clutch 24 and the saw teeth 33 of the clutch plate 25 is such that each tooth pitch corresponds to a conventional unit dose, or the like.

The dose dial sleeve 27 is wound out of the housing 3 (rotational movement and axial movement in the proximal direction) when a dose to be dispensed is increased because of its engagement with (insert 43 of) the housing 3 via the threads 41, 42. The helical groove 41 of the dose dial sleeve 27 and the internal thread 21 of the drive sleeve 19 have the same lead. This allows the dose dial sleeve 27 to extend from the housing 3 and the drive sleeve 19 to climb along the second thread 16 of the piston rod 17 in the proximal direction at the same rate (rotational movement and axial movement in the proximal direction with respect to the housing 3 and with respect to the piston rod 17).

At the limit of travel, a radial stop (not shown) on the dose dial sleeve 27 engages with a stop feature 56 provided on the insert 43 of the housing 3 to prevent further movement. During dose setting rotation of the piston rod 17 is prevented due to the opposing directions of the first and second threads 15, 16 on the piston rod 17, the first thread 15 being engaged with the nut means 11 and the second thread 16 being engaged with the drive sleeve 19.

The dose limiting member 28 which is prevented from rotating with respect to the housing 3, preferably by means of spline features (not shown), moves axially towards the proximal end of the housing 3 when the dose dial sleeve 27 rotates and moves in the proximal direction during dose setting. When a dose is set that can maximally be dispensed from the cartridge 6, the radially extending flange 34 abuts a radial stop element 60 (protrusion 58) formed on the piston rod 17, preventing the dose limiting member 28 from further proximal axial movement and both the dose dial sleeve 27 and the drive sleeve 19 from rotating further in the direction for setting a larger dose. This dose limiting mechanism will be explained in further detail below with respect to FIGS. 1*d* and 1*e*.

Should a user inadvertently dial beyond the desired dosage, the medication delivery device allows the dosage to be dialed down without dispense of medicinal product from the cartridge 6. The dose dial grip 46 is counter rotated for this purpose. This causes the system to act in reverse. The dose dial sleeve 27, the clutch 24 and the drive sleeve 19 rotate together in the reverse direction. The reverse rotation of the clutch 24 causes the saw teeth 29 and 33 of the clutch 24 and the clutch plate 25 to ride over one another to create the clicks corresponding to dialled dose reduction. Preferably the saw teeth 29 and 33 are so disposed that the circumferential extent of each saw tooth corresponds to a unit dose.

FIG. 1*a* shows the medication delivery device in a state before a first dose has been set. FIG. 1*b* shows the medication delivery device 1 according to FIG. 1*a* in a state in which a dose has been set. The dose dial sleeve 27 is extending proximally from the housing 3.

When the desired dose has been dialled, the user may then dispense this dose by depressing the button 49. This displaces the clutch 24 axially towards the distal end of the device with respect to the dose dial sleeve 27, thereby decoupling the clutch 24 from the dose dial sleeve 27. However, the clutch 24 remains keyed in rotation to the drive sleeve 19. Therefore the decoupling of the clutch 24 results in a decoupling of the dose dial sleeve 27 and the drive sleeve 19 The dose dial sleeve 27 and associated dose dial grip 46 are free to rotate, guided by the helical rib 42 of the insert 43 located in the helical groove 41 of the dose dial sleeve 27. During dose delivery the dose dial sleeve 27 is wound back into the housing 3 in the distal direction. Audible and tactile feedback or the dose dispensed is provided by the flexible arms of the clutch 24 and the internal splines of the dose dial sleeve 27 because of the rotational movement of the dose dial sleeve 27 with respect to the clutch 24.

The pressure of the user on the button 49 further results in an axial movement of the clutch 24 in the distal direction without rotation with respect to the housing 3. The axial movement of the clutch 24 moves the clutch plate 25 distally against the force of the biasing means 26 until the clutch plate 25 abuts a shoulder on the drive sleeve 19 and the clutch 24 and clutch plate 25 are engaged such that relative rotation between the clutch 24 and the clutch plate 25 is prevented, thus preventing rotation of the clutch 24 and the drive sleeve 19 with respect to the housing 3 during dose delivery. As the clutch plate 25 is splined to the dose limiting member 28 to prevent rotation of the clutch plate 25 with respect to the housing 3, the clutch plate 25, the clutch 24 and the drive sleeve 19 travel together distally but do not rotate.

The axial movement of the clutch 24 causes the drive sleeve 19 to move axially in the distal direction. The distal longitudinal axial movement of the drive sleeve 19 further causes (by means of the internal thread 21 of the drive sleeve 19 and the second thread 16 of the piston rod 17) the piston rod 17 (first threaded section 15) to rotate and thus to wind through the opening 13 in the nut means 11, thereby to advance the piston 7 in the cartridge 6.

Once the dialled dose has been dispensed, the dose dial sleeve 27 is prevented from further rotation by a plurality of rotational stop features (not shown) extending from the dose dial grip 46 engaging with stop features 55 located on the insert 43 of the housing 3. In the illustrated embodiment, the rotational stop features extend axially from the dose dial grip 46 and have an inclined end surface. The zero position is determined by the abutment of one of the axially extending edges of the rotational stop features (not shown) with a corresponding stop 55 on the insert 43.

The rotational movement of the dose dial sleeve 27 during dose delivery causes the dose limiting member 28 to move axially in a distal direction back to its initial position within the housing 3.

FIG. 1c shows the medication delivery device according to FIGS. 1a and 1b after a dose has been dispensed. The piston rod 17 and the piston 7 in the cartridge 6 have been advanced in the distal direction. The dose dial sleeve 27 and the dose limiting member 28 are in their original position with respect to the housing 3.

When the final dose has been dispensed, the spent cartridge 6 may be removed and disposed of. To remove the cartridge 6, the cartridge holder 2 is disengaged from the housing 3 by disengaging the first and second engagement means 5, 4. Once the cartridge holder 2 is disengaged from the housing 3, the spent cartridge 6 can be removed from the cartridge holder 2 and a new cartridge 6 can be placed in the cartridge holder 2.

For reusing the medication delivery device 1 it has to be reset by moving the piston rod 17 proximally into its initial position. As long as the nut means 11 is in the operational state, the proximal movement of the piston rod 17 is prevented. Therefore the nut means 11 has to be brought into the resetting state, in which it is allowed to rotate with respect to the housing 3 so that the piston rod 17 can be moved in the proximal direction.

Disengagement of the cartridge holder 2 from the housing 3 causes the locking means 9, under the force of the biasing means 14, to disengage from the nut means 11. The locking means 9 then does not prevent rotation of the nut means 11 anymore. The nut means 11 is thus not in the operational state anymore, it is in the resetting state. This allows the nut means 11 to rotate freely and therefore the piston rod 17 to be wound back up in the proximal direction.

In order to attach the cartridge holder 2 containing the new cartridge 6 on the housing 3, the piston rod 17 has to be moved axially in the proximal direction. This proximal movement may be caused by the piston 7 of the cartridge 6 abutting the end of the piston rod 17 and being moved proximally with respect to the housing 3 when the cartridge holder 2 with the cartridge 6 is moved towards the housing 3 by the user. The pushing back of the piston rod 17 by means of the piston 7 of the new cartridge 6 which is pushed against the pressure foot 18 of the piston rod 17 has the advantage, that the pressure foot 18 of the piston rod 17 already abuts the piston 7 of the cartridge 6 when the device is reset. Therefore, the priming movement of the piston rod 17 (to remove air from the cartridge 6) can be very small and the loss of medication due to priming thus be kept to a minimum. Alternatively the user may push the piston rod 17 in the proximal direction e.g. by means of a finger and then attach the cartridge holder 2 with cartridge 6 to the housing 3. As the nut means 11 (which is threadedly engaged with the piston rod 17) is free to rotate with respect to the housing 3 in the resetting state the piston rod 17 is free to rotate and translate proximally until the locking means 9 and the nut means 11 engage. The dose limiting member 28 does not affect the resetting of the piston rod 17.

Thus the dosing mechanism of the medication delivery device 1 according to the present invention is reset into a zero (or no dose delivered) position as indicated in FIG. 1a.

FIGS. 1d and 1e show the medication delivery device according to FIGS. 1a to 1c in a state in which the dose limiting member 28 and the piston rod 17 interact in order to prevent the setting of a higher dose.

The dose limiting member 28 is designed for axial movement in a proximal direction with respect to the piston rod 17 during setting of a higher dose and for axial movement in the distal direction together with the piston rod 17 during dose delivery. The dose limiting member 28 is allowed to move axially and is prevented from rotation with respect to the housing 3. It is splined to the housing 3 and is thereby prevented from rotation with respect to the housing 3. The piston rod 17 rotates during dose delivery with respect to the housing 3 and with respect to the dose limiting member 28.

The dose limiting member 28 comprises a first stop element 35 and the piston rod 17 comprises a second stop element 36, the first and second stop elements 35, 36 stopping an axial movement of the dose limiting member 28 in the proximal direction with respect to the piston rod 17 when the first and second stop elements 35, 36 catch, thereby limiting a movement of the dose dial sleeve 27 for increasing a set dose of medication to be delivered, The dose limiting member 28 is provided to stop a dose increasing movement of the dose dial sleeve 27 when the axial movement of the dose limiting member 28 is stopped. The dose limiting member 28 and the piston rod 17 only interact directly, when the first and second stop elements 35, 36 catch.

Accordingly, the dose limiting member 28 and the piston rod 17 do not interact directly during the normal use (dose setting and dose delivery) of the medication delivery device as long as the amount of medication within the cartridge 6 is sufficient. They are just moved along one another during dose setting. Only when the user attempts to set a dose which exceeds the amount of medication left in the cartridge 6, the first and second stop elements 35, 36 of the dose limiting member 28 and the piston rod 17, respectively, catch (e.g. engage or abut), resulting in a direct interaction of the dose limiting member 28 and the piston rod 17. This interaction of the piston rod 17 and the dose limiting member 28 only in this one case of the "last dose situation" of the device has the advantage, that there is also no interaction between the dose limiting member 28 and the piston rod 17 during resetting of the device (i.e. moving back the piston rod 17 to its initial position when inserting a new cartridge 6 into the device). Therefore, the dose limiting member 28 does not prevent or hinder the resetting of the medication delivery device.

The dose dial sleeve 27 is threadedly engaged with the housing 3 and therefore rotates and moves proximally with respect to the housing 3 during setting of a higher dose, rotates and moves distally with respect to the housing 3 during reducing of a set dose and rotates and moves distally with respect to the housing 3 during dose delivery.

The dose limiting member 28 is connected with the dose dial sleeve 27 via the threaded insert 53 of the dose dial sleeve 27. The dose limiting member 28 comprises an essentially tubular sleeve which is threadedly engaged with the insert 53 of the dose dial sleeve 27.

The threaded insert 53 is secured against axial movement with respect to the dose dial sleeve 27 by means of an end cap 54 secured to the distal end of the dose dial sleeve 27. The end cap 54 is secured against both rotational and axial movement with respect to the dose dial sleeve 27. The threaded engagement of the dose limiting member 28 with the insert 53 and the splined engagement of the dose limiting member 28 with the housing 3 which allows only axial movement of the dose limiting member 28 with respect to the housing 3 have the effect that the dose limiting member 28 is moved in the proximal direction (without rotation) with respect to the housing 3 and with respect to the piston rod 17 during dose setting when the set dose of medication to be delivered is increased and that the dose limiting member 28 is moved in the distal direction (without rotation) with respect to the housing during medication delivery.

The dose limiting member 28 (and its first stop element 35) therefore preferably changes its position with respect to the piston rod 17 (and its second stop element 36) during setting of a dose and keeps its relative position during the dispensing of a dose.

The lead of the thread between the dose dial sleeve 27 and the housing 3 is greater than the lead of the thread between the insert 53 and the dose limiting member 28. Therefore the distance which the dose dial sleeve 27 travels (during the setting of a dose and during the dispensing of a dose) is greater than the distance which the dose limiting member 28 travels at the same time. The maximum distance which the dose limiting member can travel proximally along the piston rod 17 is limited by the axial distance of the first and second stop members 35, 36 which preferably relates to the remaining amount of medication to be dispensed from the medication receptacle of the medication delivery device.

The dose limiting member 28 comprises an internal flange 37 which surrounds an opening 38, wherein the piston rod 17 extends through the opening 38 and wherein the internal flange 37 comprises the first stop element 35 (the abutment surface 39 of the internal flange 37). As long as the first stop element 35 does not catch the second stop element 36 of the piston rod 17, a relative axial movement of the piston rod 17 (through the opening 38 of the flange 37) and the dose limiting member 28 is allowed without interaction of the piston rod 17 and the dose limiting member 28.

The second stop element 36 is a protrusion 58 which extends radially from the piston rod 17, the axial position of the protrusion 58 on the piston rod 17 being related to the total amount of medicament to be dispensed. It is designed such that it catches the internal flange 37 of the dose limiting member 28 when the setting of a dose is attempted which exceeds the amount of medication contained in the cartridge 6, thereby stopping an axial movement of the dose limiting member 28 in the proximal direction with respect to the piston rod 17. The piston rod 17 is prevented from moving proximally at all times (except during resetting of the medication delivery device, when the cartridge holder 2 is disengaged from the housing 3 and the piston rod 17 can be moved back into its initial position).

The protrusion 58 which forms the second stop element is the end of a thread on the piston rod 17. The piston rod 17 comprises two threaded regions 15, 16, a first threaded region 15 which does not influence axial movement of the dose limiting member 28 and a second threaded region 16, wherein one end of the thread in the second threaded region 16 forms the second stop element 36. In this embodiment the cross section of the second thread 16 is larger than the cross section of the first thread 15, the first thread 15 passing through an opening 38 of the dose limiting member 28 without interaction of the piston rod 17 with the dose limiting member 28 and the second thread 16 not passing through the opening 38 but abutting the surrounding edge of the opening 38 (abutment surface 39).

The dose limiting member 28 is positioned in the same position with respect to the housing 3 prior to dose setting and after dose delivery. It moves axially in one direction during the setting of a higher dose and in the other direction during the setting of a lower dose and/or during dose delivery. The distance of axial travelling of the dose limiting member 28 in one direction with respect to the housing 3 from an initial position to the set dose position during dose setting and the distance of axial travelling of the dose limiting member 28 in the other direction with respect to the housing 3 from the set dose position to the initial position during dose delivery are essentially the same and the dose limiting member 28 and the piston rod 17 travel essentially the same distance in the distal direction during medication delivery.

FIG. 1*d* shows the medication delivery device 1 in a state in which a last dose has been set and in which the dose limiting member 28 prevents the setting of a higher dose. Similar to FIG. 1*b* the dialling of this last dose has resulted in the drive sleeve 19 being wound proximally up the piston rod 17, the dose dial sleeve 27 being wound proximally out of the housing 3 and the dose limiting member 28 also being moved in the proximal direction with respect to the housing 3. The dose limiting member 28 therefore moves proximally with respect to the piston rod 17. The movement of the dose limiting member 28 in the axial proximal direction along the piston rod 17 during dose dialling ends in the abutment of the first and second stop elements 36, 36. This abutment of the internal flange 37 on the protrusion 58 which is formed by the distal end of the second thread 15 of the piston rod 17 stops the further axial movement of the dose limiting member 28 in the proximal direction and thereby stops the further winding of the dose dial sleeve 27 out of the proximal end of the housing 3 and therefore prevents the setting of a larger dose. However, in this state the dose limiting member 28 can still be moved in the dose decreasing direction (wound back distally into the housing 3) in order to decrease the set dose. A further movement of the dose dial sleeve 27 in the dose increasing direction is stopped by the dose limiting member 28 (the axial movement of which is stopped by the abutting stop elements 35, 36) because of the threaded engagement between the dose limiting member 28 and the dose dial sleeve 27 (in the shown embodiment a threaded engagement of the dose limiting member 28 with the threaded insert 53 of the dose dial sleeve 27).

After this last dose has been delivered, the medication delivery device is in a state as shown in FIG. 1*e*. The dose limiting member 28 has moved back distally into its initial position. The piston rod 17 has at the same time moved distally (essentially the same distance as the dose limiting member 28) for medication delivery. Therefore the first and second stop elements 35, 36 have remained in their abutting state and thus still prevent an axial movement of the dose limiting member 28 in the proximal direction and thereby the a dose increasing movement of the dose dial sleeve 27 with respect to the housing 3. Accordingly it is not possible to set another dose to be dispensed when the medication delivery device is in this end-of-content position as shown in FIG. 1e. The cartridge 6 has to be replaced and the medication delivery device 1 reset in order to use the device again for medication delivery.

FIGS. 2a and 2b show schematically a cut-out of cross-section of one embodiment of a medication delivery device according to the present invention comprising at least one locking member. This delivery device can e.g. be designed as shown in FIGS. 1a to 1e.

The cut-out shows an insert 53 of a dose dial sleeve 27, a biasing means 63 and a housing 3.

The medication delivery device further comprises at least one (preferably two, three or four) locking member(s) 64 for locking the dose dial sleeve 27 with the housing 3, thereby preventing rotation of the dose dial sleeve 27 with respect to the housing 3 in a dose increasing direction, the locking member 64 being activated e.g. when the first stop element 35 (not shown) of the dose limiting member 28 (not shown) catches the second stop element 36 (not shown) of the piston rod (not shown) and when further torque is exerted on the dose dial sleeve 27 in the dose increasing direction. The catching of the two stop elements 35, 36 results in stopping the axial movement of the dose limiting member 27 in the proximal direction (as described above with reference to the embodiments shown FIGS. 1a to 1e) and thus the dose limiting member 28 stopping the dose increasing movement of the dose dial sleeve 27. Any further force/torque exerted by the user on the dose dial sleeve 27 is transferred to the at least one locking member 64 and moves the at least one locking member 64 into a locking position in which it locks the dose dial sleeve 27 with the housing 3. This locking action is an additional feature to prevent a further dose increasing movement of the dose dial sleeve 27 (the dose dial sleeve 27 being stopped by the dose limiting member 27 and by the locking member 64). However, it could also be provided as the only feature for this purpose.

The medication delivery device shown in FIGS. 2a and 2b comprises locking members 64 which are connected to the dose dial sleeve 27. The locking members 64 are separate fingers which are each connected to the dose dial sleeve 27 via a swivel axis. The locking members 64 are held in a first deactivated position (as shown in FIG. 2a) by the biasing means 63 as long as they are not activated. When the locking members 64 are activated (as shown in FIG. 2b) they are each swivelled out by means of a ramp feature 65, the locking members 64 thereby engaging at least one locking feature 66 of the housing 3. In the embodiment shown in FIGS. 2a and 2b the threaded insert 53 comprises the ramp features 65, the insert 53 being located within the dose dial sleeve 27. The dose dial sleeve 27 is allowed to perform a rotational movement about a certain angle in a dose increasing direction 67 with respect to the insert 53 when the first and second stop elements 35, 36 abut and the user exerts a force on the dose dial sleeve 27 in the dose increasing direction, thereby rotating the dose dial sleeve 27 with respect to the insert 53. This relative rotational movement moves the at least one locking member 64 over the at least one ramp feature 65 of the insert 53 (which is prevented from following the rotational movement of the dose dial sleeve 27 e.g. by a dose limiting member 28 which is engaged with the insert 53), the locking member 64 thereby swivelling out and engaging at least one locking feature 66 of the housing 3. In the embodiment shown in FIGS. 2a and 2b the locking features 66 of the housing 3 are numerous splines which run axially along the inner surface of the housing 3 and which have a saw-tooth shaped cross-section.

The function of the locking mechanism according to FIGS. 2a and 2b has been described in the context of the embodiment of the medication delivery device according to the present invention as shown in FIGS. 1a to 1e. However, such a locking mechanism can be activated by other means in a medication delivery device than by stop members and a dose limiting member. The medication delivery device can therefore comprise
    a cartridge (not shown),
    a dosing mechanism comprising
        a dose dial sleeve 27 for setting a dose of medication to be delivered and
        a dose setting limiting mechanism which prevents the setting of a dose of medication which exceeds a maximum amount of medication to be delivered from the cartridge and
    a housing 3 which houses at least part of the dosing mechanism,
wherein the dose setting limiting mechanism comprises at least one locking member 64 for locking the dose dial sleeve 27 with the housing 3, thereby preventing movement of the dose dial sleeve 27 with respect to the housing 3 in a dose increasing direction 67. The at least one locking member 64 of the present invention can be activated e.g. when two components (not shown) of the medication delivery device are moved into abutment or engagement during dose setting and when the user then exerts a force on the dose dial sleeve 27 to move it further in the dose increasing direction 67. This force is transferred to the locking member 64 in order to be activated and to be brought into a locking state in which the locking member 64 locks the dose dial sleeve 27 with the housing 3 of the dose delivery device, thereby preventing movement (preferably preventing rotation) of the dose dial sleeve 27 with respect to the housing 3 in the dose increasing direction 67.

FIG. 3 shows a cut-out of another embodiment of a medication delivery device according to the present invention comprising a locking member.

The medication delivery device comprises a locking member 64 which is a clutch ring 68. The clutch ring 68 is connected to or an integral part of the dose dial sleeve 27. Preferably, the clutch ring 68 is connected to the dose dial sleeve by laser welding. Therefore it follows each movement (axially and rotationally) of the dose dial sleeve 27. The clutch ring 68 is a toothed ring with a ring of teeth 73 which are pointing in the proximal direction.

The medication delivery device further comprises a locking feature 66 which is a locking ring 69. The locking ring 69 is splined to the housing 3 and therefore prevented from rotation with respect to the housing 3 while axial movement of the locking ring 69 is allowed. The locking ring 69 is a toothed ring with teeth 78 which are pointing in the distal direction.

An insert 74 is provided within the dose dial sleeve 27. The insert 74 is non-rotatably attached to the dose dial sleeve 27, e.g. by means of splines. The insert can move axially a certain distance with respect to the dose dial sleeve 27 as will be described below. The insert 74 carries an engaging feature 75 which is in engagement with the locking ring 69 such that the insert 74 is allowed to rotate with respect to the locking ring 69 but prevented from moving axially with respect to the locking ring 69. Therefore, the locking ring 69 follows the axial movement of the insert 74.

Furthermore, the insert 74 is threadedly engaged with a dose limiting member 28 (thread 77). The dose limiting member can only be moved axially without rotating with respect to the housing 3. A rotational movement of the insert 74 with respect to the housing moves the dose limiting member 28 axially with respect to the housing 3 due to the threaded engagement between the insert 74 and the dose limiting member 28.

The clutch ring 68 is provided as a locking member 64 for locking the dose dial sleeve 27 with the housing 3, thereby preventing further rotation of the dose dial sleeve 27 with respect to the housing 3 in a dose increasing direction, the locking member 64 being activated when the first stop element 35 of the dose limiting member 28 catches the second stop element 36 of the piston rod 17 and when a further force (a torque) is exerted on the dose dial sleeve 27 in the dose increasing direction. The catching of the two stop elements 35, 36 results in stopping the axial movement of the dose limiting member 28 in the proximal direction and thus the dose limiting member 28 stopping the dose increasing movement of the dose dial sleeve 27. Any further force/torque exerted by the user on the dose dial sleeve 27 is transferred to the at least one locking member 64 and moves the at least one locking member 64 with respect to the insert 74 and the locking feature 66 into a locking position in which it engages the locking feature 66 and thereby locks the dose dial sleeve 27 with the housing 3.

The insert 74 and the dose dial sleeve 27 are axially moveable with respect to each other, but are held in a certain axial position with respect to each other by a biasing means 76 until the first and second stop elements 35, 36 catch. Until then, the locking member 64 is held in a first deactivated position by the biasing means 76. When the two stop elements 35, 36 abut (thereby preventing a further axial movement of the dose limiting member 28 and the locking feature 66 in the proximal direction with respect to the housing 3), a further force/torque exerted by the user on the dose dial sleeve 27 in the dose increasing direction results in the dose limiting member 28 holding the insert 74 and the locking feature 66 in a certain axial position with respect to the housing while the dose dial sleeve 27 is moved in the proximal direction with respect to the insert 74 and the locking feature 66 so that it activates the locking member 64. Locking member 64 is activated by moving the locking member 64 (clutch ring 68) and the locking feature 66 (locking ring 69) into engagement (teeth 73, 78 engaged).

In this locked state a movement (i.e. a rotational and axial movement) of the locking member 64 in the dose increasing direction with respect to the housing 3 is prevented, the locking member 64 and the locking feature 66 being engaged, thereby preventing a further movement (i.e. a rotational and axial movement) of the dose dial sleeve 27 with respect to the housing 3 in a dose increasing direction.

The locking member 64 is automatically (by the force of the biasing means 76) disengaged from the locking feature 66 of the housing 3 as soon as the set dose is reduced and/or the user no longer exerts a force/torque on the dose dial sleeve 27 in the dose increasing direction (e.g. when the set dose is dispensed).

In this embodiment a biasing means 76 is preferably located between the locking member 64 and the locking feature 66 for keeping the locking member 64 and the locking feature 66 disengaged, preferably the teeth 73 of the locking member 64 and the teeth 78 of the locking feature 66 disengaged, until the locking member 64 is activated (e.g. when the first stop element 35 of the dose limiting member 28 abuts the second stop element 36 of the piston rod 17 and when a force or torque is exerted on the dose setting member 27 in the dose increasing direction).

REFERENCE NUMBERS

| | |
|---|---|
| 1 | medication delivery device |
| 2 | cartridge holder |
| 3 | housing |
| 3A | insert of the housing |
| 4 | second engagement means |
| 5 | first engagement means |
| 6 | cartridge |
| 7 | piston |
| 8 | engaging means |
| 9 | locking means |
| 10 | face teeth of locking means |
| 11 | reset element/nut means |
| 12 | face teeth of nut means |
| 13 | opening of nut means |
| 14 | biasing means |
| 15 | first thread of piston rod |
| 16 | second thread of piston rod |
| 17 | piston rod |
| 18 | pressure foot |
| 19 | drive sleeve |
| 20 | flange of drive sleeve |
| 21 | internal thread of drive sleeve |
| 22A | shoulder |
| 22B | extension |
| 23 | flange |
| 24 | clutch |
| 25 | clutch plate |
| 26 | biasing means |
| 27 | dose dial sleeve |
| 28 | dose limiting member |
| 29 | saw teeth at distal end of clutch |
| 30 | flange of clutch |
| 31 | saw teeth at proximal end of clutch |
| 32 | flexible arms |
| 33 | saw teeth of clutch plate |
| 34 | flange at distal end of dose limiting member |
| 35 | first stop element of dose limiting member |
| 36 | second stop element of piston rod |
| 37 | internal flange of dose limiting member |
| 38 | opening of internal flange |
| 39 | abutment surface of internal flange |
| 40 | window |
| 41 | outer helical thread of dose dial sleeve |
| 42 | helical thread of the insert |
| 43 | insert of the housing |
| 44 | stop features on dose dial sleeve |
| 45 | radially extending members |
| 46 | dose dial grip |
| 47 | central opening of dose dial grip |
| 48 | annular recess of dose dial grip |
| 49 | button |
| 50 | stem of button |
| 51 | head of button |
| 52 | skirt of button |
| 53 | threaded insert of dose dial sleeve |
| 54 | end cap |
| 55 | stop features on insert 43 |
| 56 | stop features on insert 43 |
| 57 | web |
| 58 | protrusion on piston rod |
| 60 | radial stop element on piston rod |
| 63 | biasing means |

-continued

| 64 | locking member |
| 65 | ramp feature |
| 66 | locking feature of the housing |
| 67 | dose increasing direction |
| 68 | clutch ring |
| 69 | locking ring |
| 73 | teeth of clutch ring |
| 74 | insert |
| 75 | engaging feature of the insert |
| 76 | biasing means |
| 77 | thread between the dose limiting member and the insert |
| 78 | teeth of the locking ring |

What is claimed is:

1. A medication delivery device comprising
a medication receptacle,
a dosing mechanism comprising
   a piston rod which is moveable in a distal direction for medication delivery
   a drive device for moving the piston rod in the distal direction for medication delivery,
   a dose setting member for setting a dose of medication to be delivered and
   a dose limiting member which prevents the setting of a dose of medication which exceeds an amount of medication contained in the medication receptacle and
a housing which houses at least part of the dosing mechanism, wherein
the dose limiting member is designed for axial movement in a proximal direction with respect to the piston rod during dose setting and
the dose limiting member comprises a first stop element and
the piston rod comprises a second stop element,
the first and second stop elements stopping an axial movement of the dose limiting member in the proximal direction with respect to the piston rod when the first and second stop elements catch,
thereby limiting a movement of the dose setting member for increasing a set dose of medication to be delivered,
wherein the dose limiting member and the piston rod only interact directly, when the first and second stop elements catch.

2. The medication delivery device according to claim 1, wherein the dose limiting member is engaged with the dose setting member, the dose limiting member stopping a movement of the dose setting member for increasing a set dose of medication to be delivered when the axial movement of the dose limiting member is stopped.

3. The medication delivery device according to claim 1, wherein the dose limiting member is coupled to or engaged with the dose setting member
   so that the dose limiting member is moved in the proximal direction with respect to the housing and with respect to the piston rod during dose setting when the set dose of medication to be delivered is increased by moving the dose setting member in a dose increasing direction and
   so that the dose limiting member is moved in the distal direction with respect to the housing during medication delivery.

4. The medication delivery device according to claim 3, wherein the dose limiting member is engaged with an internal thread of the dose setting member or engaged with a threaded insert of the dose setting member.

5. The medication delivery device according to claim 1, wherein the dose setting member is a dose dial sleeve which is threadedly engaged with the housing; and therefore rotates and moves proximally with respect to the housing during setting of a higher dose, rotates and moves distally with respect to the housing during reducing of a set dose and rotates and moves distally with respect to the housing during dose delivery.

6. The medication delivery device according to claim 1, wherein the dose limiting member comprises an essentially tubular sleeve which is threadedly engaged with the dose setting member or with an insert of the dose setting member.

7. The medication delivery device according to claim 1, wherein the dose limiting member comprises an opening, wherein the piston rod extends through the opening and wherein the first stop element is provided as a surface surrounding the opening.

8. The medication delivery device according to claim 1, wherein the first stop element is an abutment surface of an internal flange of the dose limiting member.

9. The medication delivery device according to claim 1, wherein the second stop element is a protrusion which extends radially from the piston rod, the axial position of the protrusion on the piston rod being related to the total amount of medicament to be dispensed.

10. The medication delivery device according to claim 1, wherein the second stop element is the end of a thread on the piston rod.

11. The medication delivery device according to claim 1, wherein the piston rod comprises two threaded regions, a first threaded region which does not influence axial movement of the dose limiting member and a second threaded region, wherein one end of a thread in the second threaded region forms the second stop element.

12. The medication delivery device according to claim 1, wherein the dose limiting member is allowed to move axially and is prevented from rotation with respect to the housing.

13. The medication delivery device according to claim 12, wherein the dose limiting member is splined to the housing and is thereby prevented from rotation with respect to the housing.

14. The medication delivery device according to claim 1, wherein the piston rod comprises two threaded regions, the two threaded regions having threads which are oppositely disposed.

15. The medication delivery device according to claim 1, further comprising a drive device which is engaged with the piston rod and releasably engaged with the dose setting member.

16. The medication delivery device according to claim 15, wherein the piston rod comprises two threaded regions, the two threaded regions having threads which are oppositely disposed, wherein a second threaded region is provided for threaded engagement with the drive device.

17. The medication delivery device according to claim 1, further comprising a clutch means located between the dose setting member and the drive device which is provided to releasably couple the drive device with the dose setting member, wherein when the dose setting member and the drive device are coupled, both are allowed to rotate with respect to the housing and when the dose setting member and the drive device are decoupled, rotation of the dose setting member with respect to the housing is allowed, whilst rotation of the drive device with respect to the housing is not allowed and axial movement of the drive device is allowed so that a force is transferred to the piston rod in the distal direction.

18. The medication delivery device according to claim 1, wherein the dose limiting member comprises a tubular part which surrounds the piston rod, a drive sleeve and a clutch means and which is surrounded by the dose setting member.

19. The medication delivery device according to claim 1, wherein the dosing mechanism comprises at least one locking member for locking the dose setting member with the housing, thereby preventing rotation of the dose setting member with respect to the housing in a dose increasing direction, the locking member being activated when the first stop element of the dose limiting member catches the second stop element of the piston rod and when a force is exerted on the dose setting member in the dose increasing direction.

20. The medication delivery device according to claim 19 comprising at least one locking member which interacts directly with or is connected to the dose setting member and/or which interacts directly with or is connected to an insert of the dose setting member, which insert is in engagement with the dose limiting member and designed for movement with respect to the dose setting member.

21. The medication delivery device according to claim 20 comprising at least one locking member which is a separate part and which is connected to the dose setting member via a swivel axis.

22. The medication delivery device according to claim 19, wherein by an insert of the dose setting member, the dose setting member being allowed to perform a movement in a dose increasing direction with respect to the insert when the first and second stop elements abut, thereby moving the at least one locking member and at least one locking feature of the housing into engagement.

23. The medication delivery device according to claim 22, wherein the insert is a threaded insert which is threadedly engaged with the dose limiting member.

24. The medication delivery device according to claim 19, wherein the at least one locking member is swivelled out by means of at least one ramp feature when activated, thereby engaging at least one locking feature of the housing.

25. The medication delivery device according to claim 24, wherein an insert of the dose setting member comprises the at least one ramp feature, the dose setting member being allowed to perform a rotational movement in a dose increasing direction with respect to the insert, thereby moving the at least one ramp feature along the at least one locking member, the locking member thereby swivelling out and engaging the at least one locking feature of the housing.

26. The medication delivery device according to claim 19, wherein the at least one locking member or the at least one locking feature of the housing is held in a first deactivated position by a biasing means.

27. The medication delivery device according to claim 25, wherein the at least one locking member or the at least one locking feature of the housing is held in a first deactivated position by a biasing means.

28. The medication delivery device according to claim 19, comprising at least one locking member which is an integral part of an insert of the dose setting member, the locking member extending through an opening in the dose setting member, the dose setting member being allowed to perform a rotational movement in the dose increasing direction with respect to the insert, thereby moving an edge of the opening against the locking member, the locking member thereby swivelling out and engaging a locking feature of the housing.

29. The medication delivery device according to claim 19, wherein the at least one locking member is engaged with grooves or splines in the housing when the locking member is activated, thereby preventing a movement of the dose setting member with respect to the housing in a dose increasing direction.

30. The medication delivery device according to claim 19, wherein the at least one locking member is a hook which is hooked into at least one hooking feature of the housing when the locking member is activated, thereby preventing a movement of the dose setting member with respect to the housing in a dose increasing direction.

31. The medication delivery device according to claim 19, having a locking member comprising at least one tooth for engaging a locking feature of the housing, the locking member being connected to or interacting directly with the dose setting member and the locking feature being connected to or interacting directly with the housing or with an insert of the housing such that a movement of the locking feature with respect to the housing in a dose increasing direction is prevented, thereby preventing a movement of the dose setting member with respect to the housing in a dose increasing direction when the locking member and the locking feature are engaged.

32. The medication delivery device according to claim 31, wherein the locking member is a first toothed ring connected to a dose dial sleeve and the locking feature is a second toothed ring, the second toothed ring being prevented from rotation with respect to the housing, thereby preventing rotation of the dose dial sleeve with respect to the housing when the two toothed rings are engaged.

33. The medication delivery device according to claim 32, wherein the dose dial sleeve has a threaded insert which is engaged with the dose limiting member, the second toothed ring being prevented from moving axially with respect to the threaded insert and the threaded insert being provided for axial movement with respect to the dose dial sleeve when the first and second stop members catch and a further force is exerted on the dose dial sleeve in a dose increasing direction, the first and second toothed rings thereby being moved into engagement.

34. The medication delivery device according to claim 19, wherein a biasing means is located between the locking member and a locking feature of the housing for keeping the locking member and the locking feature disengaged until the locking member is activated.

35. The medication delivery device according to claim 1, further comprising a cartridge which contains the medication, the cartridge comprising a piston which is moved in a distal direction by the piston rod for medication delivery, wherein the dose limiting member is provided to prevent setting of a dose of medication which exceeds the amount of medication left in the cartridge.

* * * * *